(12) United States Patent
Evtimov et al.

(10) Patent No.: US 12,281,150 B2
(45) Date of Patent: Apr. 22, 2025

(54) T CELL DISEASE TREATMENT TARGETING TAG-72

(71) Applicant: CARTHERICS PTY. LTD., Carlton (AU)

(72) Inventors: Vera Evtimov, Carlton (AU); Richard Boyd, Carlton (AU); Ian Nisbet, Carlton (AU); Miles Prince, Carlton (AU); Alan Trounson, Carlton (AU)

(73) Assignee: CARTHERICS PTY. LTD., Carlton (AU)

(*) Notice: Subject to any disclaimer, the term of this patent is extended or adjusted under 35 U.S.C. 154(b) by 1142 days.

(21) Appl. No.: 16/970,790

(22) PCT Filed: Feb. 18, 2019

(86) PCT No.: PCT/AU2019/050129
§ 371 (c)(1),
(2) Date: Aug. 18, 2020

(87) PCT Pub. No.: WO2019/161439
PCT Pub. Date: Aug. 29, 2019

(65) Prior Publication Data
US 2021/0085715 A1    Mar. 25, 2021

Related U.S. Application Data

(60) Provisional application No. 62/634,366, filed on Feb. 23, 2018.

(51) Int. Cl.
| | |
|---|---|
| *A61P 35/00* | (2006.01) |
| *A61K 39/00* | (2006.01) |
| *C07K 14/705* | (2006.01) |
| *C07K 14/725* | (2006.01) |
| *C07K 16/30* | (2006.01) |
| *C12N 5/0783* | (2010.01) |

(52) U.S. Cl.
CPC .... *C07K 14/70507* (2013.01); *A61K 39/4611* (2023.05); *A61K 39/4631* (2023.05); *A61K 39/464469* (2023.05); *A61P 35/00* (2018.01); *C07K 14/7051* (2013.01); *C07K 14/70521* (2013.01); *C07K 16/3092* (2013.01); *C12N 5/0636* (2013.01); *A61K 2239/48* (2023.05)

(58) Field of Classification Search
None
See application file for complete search history.

(56) References Cited

U.S. PATENT DOCUMENTS

| | | | |
|---|---|---|---|
| 5,530,101 A | 6/1996 | Queen et al. | |
| 5,565,332 A | 10/1996 | Hoogenboom et al. | |
| 5,585,089 A | 12/1996 | Queen et al. | |
| 8,835,167 B2 | 9/2014 | Kashmiri et al. | |
| 2015/0126559 A1* | 5/2015 | Balzarini | C07D 333/36 546/281.4 |

FOREIGN PATENT DOCUMENTS

| | | |
|---|---|---|
| EP | 0 239 400 A2 | 9/1987 |
| EP | 0 519 596 A1 | 12/1992 |
| EP | 0 592 106 A1 | 4/1994 |
| WO | 91/09967 A1 | 7/1991 |
| WO | 92/22653 A1 | 12/1992 |
| WO | 98/18809 A1 | 5/1998 |
| WO | 2004/003155 A2 | 1/2004 |
| WO | 2005/021594 A2 | 3/2005 |
| WO | 2006/116076 A2 | 11/2006 |
| WO | 2011/086179 A1 | 7/2011 |
| WO | 2015/120187 A1 | 8/2015 |
| WO | 2017/088012 A1 | 6/2017 |
| WO | 2017/141243 A1 | 8/2017 |

OTHER PUBLICATIONS

Vallera et al. 2013; Cancer Biother Radiopharm 28: 274-282 Heterodimeric Bispecific Single-Chain Variable-Fragment Antibodies Against EpCAM and CD16 Induce Effective Antibody-Dependent Cellular Cytotoxicity Against Human Carcinoma Cells.*
Ngo, in The Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*
Application/Control No. 15/778,836 pp. 1-20, Apr. 21, 2021.*
Chen et al., Immunol. Lett. vol. 77, pp. 17-23, 2001, Enhancement of antigen-presenting ability of B lyphoma cells by immunostimulatory CpG-oligonucleotides and anti-CD40 antibody.*
Chang D-K et al., "Humanization of an Anti-CCR4 Antibody that Kills Cutaneous T-Cell Lymphoma Cells and Abrogates Suppression by T-Regulatory Cells", Molecular Cancer Therapeutics 11)11):2451-2461 (Nov. 2012).
European Extended Supplementary Search Report dated Oct. 28, 2021 received in European Application No. 19 75 7740.6.
Chan D V et al., "A Recombinant scFv-FasLext as a Targeting Cytotoxic Agent Against Human Jurkat-Ras Cancer", Journal of Biomedical Science 20:16 (Mar. 2013).
Dotti G. et al., "Design and Development of Therapies Using Chimeric Antigen Receptor-Expressiong T Cells", Immunol Rev. 257(1):1-35 (Jan. 2014).
Ferreira J.A. et al., "Overexpression of Tumour-Associated Carbohydrate Antigen Sialyl-Tn in Advanced Bladder Tumours", Molecular Oncology 7:719-731 (2013).

(Continued)

*Primary Examiner* — Mark L Shibuya
(74) *Attorney, Agent, or Firm* — Scully, Scott, Murphy & Presser, P.C.

(57) ABSTRACT

This disclosure relates to treatment of T cell diseases, particularly T cell lymphomas (TCLs) including, in particular, cutaneous T cell lymphomas (CTCLs) such as Sezary Syndrome (SS) and mycosis fungoides (MF), by targeting tumor-associated glycoprotein-72 (TAG-72).

18 Claims, 27 Drawing Sheets
(15 of 27 Drawing Sheet(s) Filed in Color)
Specification includes a Sequence Listing.

(56) References Cited

OTHER PUBLICATIONS

Hege K.M. et al., "Safety, Tumor Trafficking and Immunogenicity of Chimeric Antigen Receptor (CAR)-T Cells Specific for TAG-72 in Colorectal Cancer", Journal for ImmunoTherapy of Cancer 5:22 (2017).
Lazar G.A. et al., "Engineered Antibody Fc Variants With Enhanced Effector Function", PNAS 103(11):4005-4010 (Mar. 14, 2006).
Molinolo A. et al., "Enhanced Tumor Binding Using Immunohistochemical Analyses by Second Generation Anti-Tumor-Associated Glycoprotein 72 Monoclonal Antibodies Versus Monoclonal Antibody B72.3 in Human Tissue", Cancer Research 50:1291-1298 (Feb. 15, 1990).
Munckley J., "The Role of Sialyl-Tn in Cancer", International Journal of Molecular Sciences 17:275 (2016).
Nicolet C.M. et al., "TAG-72-Reactive Antibody CD49 Recognizes Molecules Expressed by Hematopoietic Cell Lines", Tumor Biology 18:356-366 (Feb. 1997).
Oberschmidt O. et al., "Redirected Primary Human Chimeric Antigen Receptor Natural Killer Cells as an "Off-the-Shelf Immunotherapy" for Improvement in Cancer Treatment", Frontiers in Immunology 8:654 (Jun. 2017).
Ogata S. et al., "Different Modes of Sialyl-Tn Expression During Malignant Transformation of Human Colonic Mucosa", Glycoconjugate Journal 15:29-35 (1998).
Ruiter D.J. et al., Application of Monoclonal Antibodies in Tumor Pathology, Martinus Nijhoff Publishers (1987).
Sharifzadeh Z. e al., "Genetically Engineered T Cells Bearing Chimeric Nanoconstructed Receptors Harboring TAG-72-Sepcific Camelid Single Domain Antibodies as Targeting Agents", Cancer Letters 334(2):237-244 (Jul. 2013).
Sheer D.G. et al., "Purification and Composition of the Human Tumor-Associated Glycoprotein (TAG-72) Defined by Monoclonal Antibodies CD49 and B72.3", Cancer Research 48:6811-6818 (Dec. 1, 1988).
Schmohl J U. et al., "Enhanced ADCC and NK Cell Activation of an Anticarcinoma Bispecific Antibody by Genetic Insertion", Molecular Therapy 24(7):1312-1322 (Jul. 2016).
International Search Report and Written Opinion dated Jan. 24, 2020 received in International Application No. PCT/AU2019/050129.
International Search Report dated May 1, 2019 received in International Application No. PCT/AU2019/050129.
Persson N. et al., "Epitope Mapping of a New Anti-Tn Antibody Detecting Gastric Cancer Cells", Glycobiology 27(7):635-645 (2017).
European Communication dated Jan. 12, 2024 received in European Patent No. 3755370, transmitting a Third Party Observation.
Kumagai I. et al., Drug Delivery System 23(5):518-525 (2008), together with an English-language abstract.
Japanese Notice of Reasons for Rejection dated Dec. 26, 2022 received in Japanese Patent Application No. 2020-543504, together with an English-language translation.
Zhang S., "Progress of Tumor Immunotherapy", Peking Union Medical College Press, pp. 179-180 (Apr. 30, 2017), (in Chinese, the relevance of which is discussed on p. 5 of the English translation of the Chinese Office Action dated Dec. 20, 2024).
Chinese Office Action dated Dec. 20, 2024 received in Chinese Application No. 201980013770.0, together with an English-language translation.

* cited by examiner

A.

B.

C.

D.

E.

F.

G.

H.

I.

J.

K.

L.

M.

N.

O.

P.

Q.

R.

S.

T.

U.

V.

| | Patient 7 | Patient 8 | Patient 9 | Patient 10 | Patient 11 | Exemplar positive staining |
|---|---|---|---|---|---|---|
| H & E | 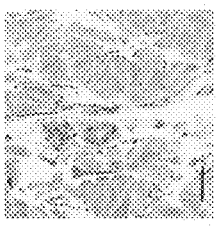 | 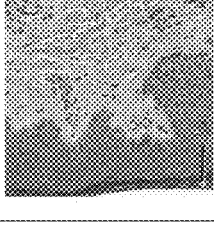 | 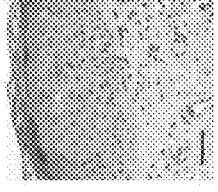 | 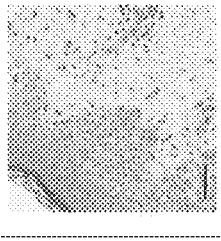 |  | n/a |
| TAG-72 | 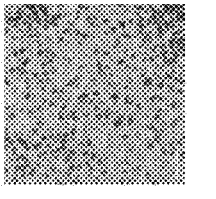 |  | 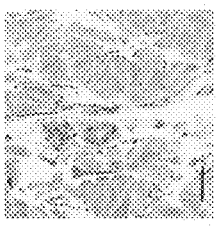 | 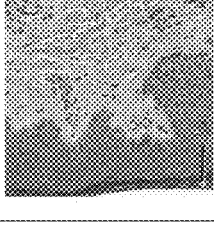 | 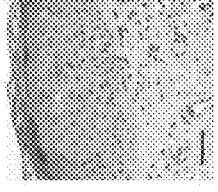 | 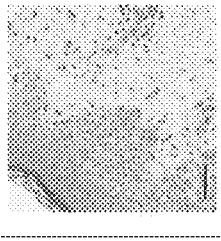 |
| CD3 | 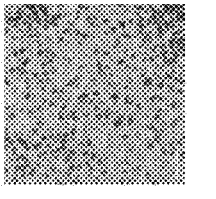 | n/a |  | 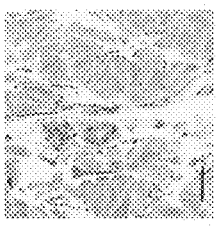 | 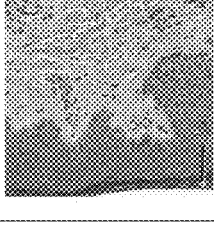 | 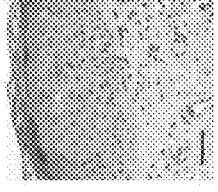 |
FIG. 4A. (continued)

| Patient sample | Infiltrating TAG-72+ cells (Y/N) | Frequency of CD3+/TAG-72+ circulating cells (%viable) |
| --- | --- | --- |
| 01 | Y | 14.19 |
| 02 | N | n/a |
| 03 | Y | 14.3 |
| 04 | N | 9.93 |
| 05 | N | n/a |
| 06 | N | 12.62 |
| 07 | N | 3.62 |
| 08 | N | 8.69 |
| 09 | N | 25.59 |
| 10 | Y | n/a |
| 11 | Y | n/a |

FIG. 4B.

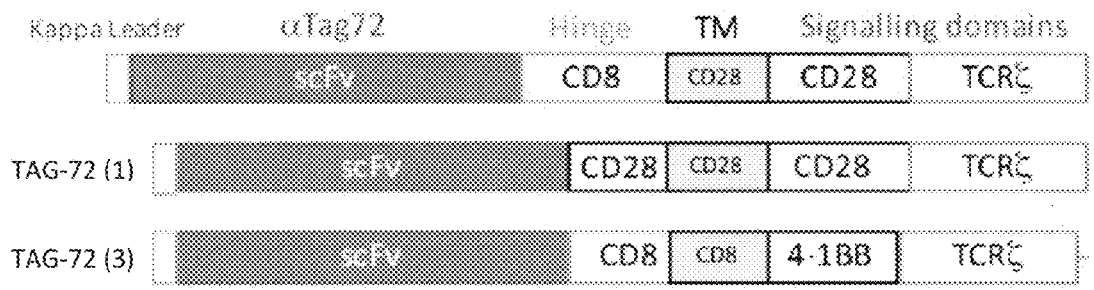

FIG. 5A

```
                                                              cag
                                                              Q
gtgcagctgcagcagagcgacgccgagctggtgaagcccggcgccagcgtgaagatcagc
 V  Q  L  Q  Q  S  D  A  E  L  V  K  P  G  A  S  V  K  I  S
tgcaaggccagcggctacaccttcaccgaccagcatcactgggtgaagcagaacccc
 C  K  A  S  G  Y  T  F  T  D  H  A  I  H  W  V  K  Q  N  P
gagcagggcctggagtggatcggctacttcagccccggcaacgacgacttcaagtacaac    TAG72
 E  Q  G  L  E  W  I  G  Y  F  S  P  G  N  D  D  F  K  Y  N     VH
gagcgcttcaagggcaaggccaccctgaccgccgacaagagcagcagcaccgcctacctg
 E  R  F  K  G  K  A  T  L  T  A  D  K  S  S  S  T  A  Y  L
cagctgaacagcctgaccagcgaggacagcgccgtgtacttctgcacccgcagcctgaac
 Q  L  N  S  L  T  S  E  D  S  A  V  Y  F  C  T  R  S  L  N
atggcctactggggccagggcaccagcgtgaccgtgagcagcggcggcggcggcagcggc
 M  A  Y  W  G  Q  G  T  S  V  T  V  S  S  G  G  G  G  S  G    GS linker
ggcggcggcagcggcggcggcggcagcgacatcgtgatgacccagagccccagcagcctg
 G  G  G  S  G  G  G  G  S  D  I  V  M  T  Q  S  P  S  S  L
cccgtgagcgtgggcgagaaggtgaccctgagctgcaagagcagccagagcctgctgtac
 P  V  S  V  G  E  K  V  T  L  S  C  K  S  S  Q  S  L  L  Y
agcggcaaccagaagaactacctggcctggtaccagcagaagcccggccagagccccaag    TAG72
 S  G  N  Q  K  N  Y  L  A  W  Y  Q  Q  K  P  G  Q  S  P  K     VL
ctcctgatctactgggccagcacccgcgagagcggcgtgcccgaccgcttcaccggcagc
 L  L  I  Y  W  A  S  T  R  E  S  G  V  P  D  R  F  T  G  S
ggcagcggcaccgacttcaccctgagcatcagcagcgtggagaccgaggacctggccgtg
 G  S  G  T  D  F  T  L  S  I  S  S  V  E  T  E  D  L  A  V
tactactgccagcagtactacagctaccccctgaccttcggcgccggcaccaagctggtg
 Y  Y  C  Q  Q  Y  Y  S  Y  P  L  T  F  G  A  G  T  K  L  V
ctgaagcgc
 L  K  R
```

B.         S5 PBMCs alone

C. SS PBMCs + NT PBMCs

D. SS PBMCs + αTAG-72 CAR-T

D.

E.

SEQUENCE LISTING

<160> NUMBER OF SEQ ID NOS: 17

<210> SEQ ID NO 1
<211> LENGTH: 732
<212> TYPE: DNA
<213> ORGANISM: Artificial Sequence
<220> FEATURE:
<223> OTHER INFORMATION: DNA coding for TAG-72 scFV

<400> SEQUENCE: 1

```
caggtgcagc tgcagcagag cgacgccgag ctggtgaagc ccggcgccag cgtgaagatc      60
agctgcaagg ccagcggcta caccttcacc gaccacgcca tccactgggt gaagcagaac     120
cccgagcagg gcctggagtg gatcggctac ttcagccccg gcaacgacga cttcaagtac     180
aacgagcgct tcaagggcaa ggccaccctg accgccgaca gagcagcag caccgcctac     240
ctgcagctga acagcctgac cagcgaggac agcgccgtgt acttctgcac ccgcagcctg     300
aacatggcct actggggcca gggcaccagc gtgaccgtga gcagcggcgg cggcggcagc     360
ggcggcggcg gcagcggcgg cggcggcagc gacatcgtga tgacccagag ccccagcagc     420
ctgcccgtga gcgtgggcga aaggtgacc ctgagctgca agagcagcca gagcctgctg     480
tacagcggca accagaagaa ctacctggcc tggtaccagc agaagcccgg ccagagcccc     540
aagctcctga tctactgggc cagcacccgc gagagcggcg tgcccgaccg cttcaccggc     600
agcggcagcg gcaccgactt caccctgagc atcagcagcg tggagaccga ggacctggcc     660
gtgtactact gccagcagta ctacagctac cccctgacct tcggcgccgg caccaagctg     720
gtgctgaaagc gc                                                         732
```

<210> SEQ ID NO 2
<211> LENGTH: 244
<212> TYPE: PRT
<213> ORGANISM: Artificial Sequence
<220> FEATURE:
<223> OTHER INFORMATION: Protein sequence of TAG-72 scFV

<400> SEQUENCE: 2

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Ser Pro Ser Ser Leu Pro Val Ser
    130                 135                 140

Val Gly Glu Lys Val Thr Leu Ser Cys Lys Ser Ser Gln Ser Leu Leu
145                 150                 155                 160

Tyr Ser Gly Asn Gln Lys Asn Tyr Leu Ala Trp Tyr Gln Gln Lys Pro 165                 170                 175
Gly Gln Ser Pro Lys Leu Leu Ile Tyr Trp Ala Ser Thr Arg Glu Ser
            180                 185                 190

Gly Val Pro Asp Arg Phe Thr Gly Ser Gly Ser Gly Thr Asp Phe Thr
        195                 200                 205

Leu Ser Ile Ser Ser Val Glu Thr Glu Asp Leu Ala Val Tyr Tyr Cys
    210                 215                 220

Gln Gln Tyr Tyr Ser Tyr Pro Leu Thr Phe Gly Ala Gly Thr Lys Leu
225                 230                 235                 240

Val Leu Lys Arg

<210> SEQ ID NO 3
<211> LENGTH: 60
<212> TYPE: PRT
<213> ORGANISM: Artificial Sequence
<220> FEATURE:
<223> OTHER INFORMATION: CD8 hinge protein sequence

<400> SEQUENCE: 3

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu
    50                  55                  60

<210> SEQ ID NO 4
<211> LENGTH: 24
<212> TYPE: PRT
<213> ORGANISM: Artificial Sequence
<220> FEATURE:
<223> OTHER INFORMATION: CD8 TM protein sequence

<400> SEQUENCE: 4

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 5
<211> LENGTH: 39
<212> TYPE: PRT
<213> ORGANISM: Artificial Sequence
<220> FEATURE:
<223> OTHER INFORMATION: CD28 hinge protein sequence

<400> SEQUENCE: 5

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 6
<211> LENGTH: 39
<212> TYPE: PRT
<213> ORGANISM: Artificial Sequence
<220> FEATURE:

<223> OTHER INFORMATION: CD28 hinge protein sequence with C to S
      substitution

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Ser Pro Ser Pro Leu
            20                  25                  30

Phe Pro Gly Pro Ser Lys Pro
            35

<210> SEQ ID NO 7
<211> LENGTH: 27
<212> TYPE: PRT
<213> ORGANISM: Artificial Sequence
<220> FEATURE:
<223> OTHER INFORMATION: CD28 TM protein sequence

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: CD28 TM with C to S substitution

<400> SEQUENCE: 8

Phe Trp Val Leu Val Val Val Gly Gly Val Leu Ala Ser Tyr Ser Leu
1               5                   10                  15

Leu Val Thr Val Ala Phe Ile Ile Phe Trp Val
            20                  25

<210> SEQ ID NO 9
<211> LENGTH: 41
<212> TYPE: PRT
<213> ORGANISM: Artificial Sequence
<220> FEATURE:
<223> OTHER INFORMATION: CD28 signalling domain protein sequence

<400> SEQUENCE: 9

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 10
<211> LENGTH: 42
<212> TYPE: PRT
<213> ORGANISM: Artificial Sequence
<220> FEATURE:
<223> OTHER INFORMATION: 4-1BB signalling domain protein sequence

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe

```
                    20                  25                  30
Pro Glu Glu Glu Glu Gly Gly Cys Glu Leu
        35                  40

<210> SEQ ID NO 11
<211> LENGTH: 112
<212> TYPE: PRT
<213> ORGANISM: Artificial Sequence
<220> FEATURE:
<223> OTHER INFORMATION: TCR zeta signalling domain protein sequence

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 12
<211> LENGTH: 5
<212> TYPE: PRT
<213> ORGANISM: Artificial Sequence
<220> FEATURE:
<223> OTHER INFORMATION: TAG-72 VH CDR1

<400> SEQUENCE: 12

Asp His Ala Ile His
1               5

<210> SEQ ID NO 13
<211> LENGTH: 17
<212> TYPE: PRT
<213> ORGANISM: Artificial Sequence
<220> FEATURE:
<223> OTHER INFORMATION: TAG-72 VH CDR2

<400> SEQUENCE: 13

Tyr Phe Ser Pro Gly Asn Asp Asp Phe Lys Tyr Asn Glu Arg Phe Lys
1               5                   10                  15

Gly

<210> SEQ ID NO 14
<211> LENGTH: 6
<212> TYPE: PRT
<213> ORGANISM: Artificial Sequence
<220> FEATURE:
<223> OTHER INFORMATION: TAG-72 VH CDR3

<400> SEQUENCE: 14

Ser Leu Asn Met Ala Tyr
1               5

<210> SEQ ID NO 15
```

```
<211> LENGTH: 17
<212> TYPE: PRT
<213> ORGANISM: Artificial Sequence
<220> FEATURE:
<223> OTHER INFORMATION: TAG-72 VL CDR1

<400> SEQUENCE: 15

Lys Ser Ser Gln Ser Leu Leu Tyr Ser Gly Asn Gln Lys Asn Tyr Leu
1               5                   10                  15

Ala

<210> SEQ ID NO 16
<211> LENGTH: 7
<212> TYPE: PRT
<213> ORGANISM: Artificial Sequence
<220> FEATURE:
<223> OTHER INFORMATION: TAG-72 VL CDR2

<400> SEQUENCE: 16

Trp Ala Ser Thr Arg Glu Ser
1               5

<210> SEQ ID NO 17
<211> LENGTH: 9
<212> TYPE: PRT
<213> ORGANISM: Artificial Sequence
<220> FEATURE:
<223> OTHER INFORMATION: TAG-72 VL CDR3

<400> SEQUENCE: 17

Gln Gln Tyr Tyr Ser Tyr Pro Leu Thr
1               5
```

T CELL DISEASE TREATMENT TARGETING TAG-72

CROSS REFERENCE TO RELATED APPLICATION

This application claims the benefit of priority from U.S. Provisional Application No. 62/634,366, filed Feb. 23, 2018, the entire contents of which are incorporated herein by reference.

FIELD OF THE DISCLOSURE

This disclosure relates to treatment of T cell diseases, particularly T cell lymphomas (TCLs) including, in particular, cutaneous T cell lymphomas (CTCLs) such as Sezary Syndrome (SS) and mycosis fungoides (MF), by targeting tumor-associated glycoprotein-72 (TAG-72).

INCORPORATION BY REFERENCE OF SEQUENCE LISTING

The Sequence Listing in the ASCII text file, named as 35478 Sequence Listing.txt of 10 KB, created on Aug. 18, 2020, is incorporated herein by reference.

BACKGROUND ART

T cell lymphomas and leukemias are rare hematological diseases. TCL is a class of non-Hodgkin's lymphoma that is caused by a T cell mutation. It includes T-lymphoblastic lymphoma/leukemia and peripheral T cell lymphomas (PTCL), which develop away from the thymus. PTCL includes a number of subtypes, some of which are more aggressive (faster growing) and others indolent (slow growing). CTCLs, which originate in the skin, are generally indolent (slow growing) forms of PTCL. In CTCL, the cancerous T cells form cutaneous lesions before spreading to other parts of the body. SS is a particular form of CTCL in which the T cells carry pathological levels of mucopolysaccharides. The primary manifestation of SS is in the skin. Treatment options for CTCL are currently limited to histone deacetylase (HDAC) inhibitors, phototherapy and chemotherapy. Remission rates are around 30% but remissions are not durable. There is a major need for new treatment options. Recent innovations in immunotherapy, such as monoclonal antibodies, antibody-drug conjugates (ADCs) and CAR-T cells, have opened up potential new approaches for the treatment of TCL. However, the development of such treatments is dependent on being able to identify specific markers on the TCL cells that are (essentially) absent on normal cells.

TAG-72 has been established as a marker for adenocarcinomas and has also been identified as a potential target for CAR-T cells in certain solid tumors (Dotti et al., *Immunol Rev* 257:1-35 (2014)). A clinical trial using TAG-72-targeted CAR-T cells has been conducted in patients with colorectal cancer (Hege et al., *J Immunother Cancer* 5:22 (2017). Potential targets for CAR-T cells in hematological malignancies (which include CTCL) have also been identified (Dotti et al., supra). TAG-72 has not been considered a potential target for hematological malignancies (Dotti et al., supra) since its expression has not been reported in such malignancies. For example, in a study on multiple cell types, TAG-72 was undetectable in 10/10 lymphoma samples (Rutter, Fleuren and Warnaar (eds), *Application of Monoclonal Antibodies in Tumor Pathology*, Martinus Nighoff Publishers (1987)). Since the majority of lymphomas are B cell lymphomas, it is likely that most of the lymphoma samples used in this study were B cell lymphomas. TAG-72 has been reported to be expressed on some hematopoietic cell lines, such as the Jurkat T cell line (Nicolet et al, *Tumour Biol* 18:356-366 (1997)). However, expression of tumor-associated antigens (TAAs) in cell lines is not necessarily reflective of the parental tumor, and there are no reports that TAG-72 has been detected on tumor cells isolated from patients with blood-based cancers or in association with any hematologic tumor.

SUMMARY OF THE DISCLOSURE

In one aspect, this disclosure provides a method of treating TCL, including particularly CTCL, in a patient comprising administering to the patient an agent targeting TAG-72.

In various embodiments, an agent targeting TAG-72 comprises a cell expressing a CAR specific for TAG-72. In some embodiments, the cell is a T cell, such as a γδ TCR T cell, a αβTCR T cell, an NKT cell, or a MAIT (Mucosal associated invariant T) cell; and in other embodiments, the cell is an NK cell. In some embodiments, the CAR comprises a TAG-72 recognition moeity, e.g., an scFv having the amino acid sequence of SEQ ID NO: 2. In some embodiments, the CAR comprises a signal transduction domain that contains the intracellular signaling domain of CD3-zeta; and in specific embodiments, the signal transduction domain further comprises the intracellular costimulatory domain of CD28, 4-1 BB, or CD2. As further described herein, the TAG-72 recognition moeity can be linked to the signal transduction domain through a hinge and a transmembrane domain.

In some embodiments, an agent targeting TAG-72 comprises an antibody specific for TAG-72, or an antigen-binding fragment thereof. In some embodiments, the antibody or antigen-binding fragment is conjugated to a cytotoxic agent. In some embodiments, the cytotoxic agent is a small molecule compound. In some embodiments, the antibody is associated with enhanced ADCC activity. In some embodiments, the antibody is a bispecific antibody; for example, a bispecific antibody that binds to a receptor on a T cell, an NK cell, or a macrophage.

In some embodiments, the CTCL is Sezary Syndrome ("SS"). In some embodiments, the CTCL is a non-SS form, such as anaplastic large-cell lymphoma, erythrodermic mycosis fungoides and follicular trophic mycosis fungoides.

In some embodiments, the treatment method disclosed herein is given to a patient who has been identified, prior to the treatment, as having an increased level of TAG-72 expressing T cells in the blood or an increased level of soluble TAG-72 in the blood, as compared to controls.

In another aspect, this disclosure is directed to a TAG-72 targeting agent for use in the treatment of TCL including, in particular, CTCL.

In a further aspect, this disclosure provides a method of diagnosing or characterizing a TCL patient comprising detecting the level of TAG-72 expressing T cells or the level of soluble TAG-72 in the blood of the patient and comparing to a control level. In some embodiments, the level of TAG-72 expressing T-cells in a patient is determined by isolating T-cells from the blood of the patient and assessing the isolated T-cells for TAG-72 expression. In some embodiments, the TAG-72 expression is assessed by using an antibody directed against TAG-72. In some embodiments, the T-cells are isolated from the blood of the patient based on their expression of CD3. In other embodiments, additional markers (e.g., CD4+, CD45RO+, and CD5+) can be included in isolating the T-cells from the blood.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4B. TAG-72 can be expressed in circulating and/or cutaneous infiltrating cells in TCL patients. Flow cytometric analysis of circulating T cells or immunohistochemistry of skin biopsies were performed as previously described. Comparative expression levels for the patients from FIG. 4A are summarized in FIG. 4B.

FIG. 5A. Schematic diagram of three TAG-72-specific CAR-T constructs showing different combinations of hinge, transmembrane (TM) and signalling domains linked to the scFv specific for TAG-72. The studies described in the Examples utilized CAR-T cells expressing either of two of these constructs, designated TAG-72 (1) and TAG-72 (3).

FIG. 5B. The nucleotide sequence (SEQ ID NO: 1) and amino acid sequence (SEQ ID NO: 2) of the scFv domain incorporated into the TAG-72-specific CAR constructs TAG-72 (1) and TAG-72 (3). The components of the TAG-72-specific scFV domain are also denoted: TAG-72 VH (the heavy chain variable region), GS linker (in bold italics), and TAG-72 VL (the light chain variable region).

In FIGS. 9G and 9H, data are pooled from 36 disease patients (G) and 10 healthy individuals (H) from FIG. 2. n.s.=non-significant;  represents p<0.01; * represents p<0.001 and **** represents p<0.0001 in paired t-test.

DETAILED DESCRIPTION

Figure 1A:
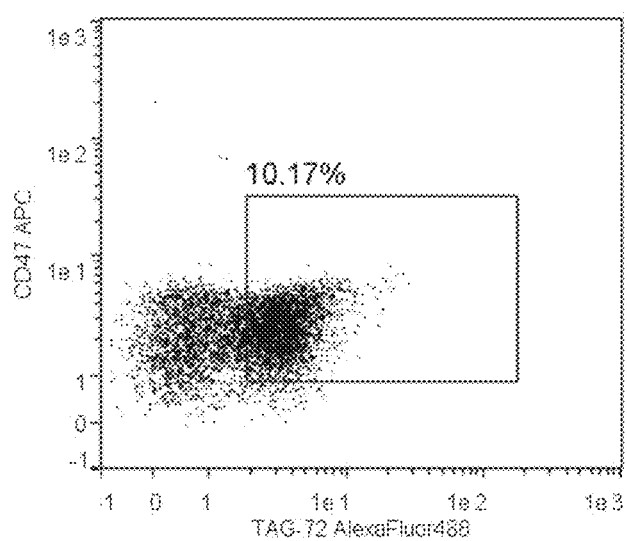
FIGS. 1A-1M. Sezary Syndrome PBMCs express the tumor-associated antigen TAG-72, as demonstrated by flow cytometry. TAG-72 was overexpressed in all patient samples (A-I) analyzed compared to healthy donor cells (J-M). Figures represent population frequency as percent of total events analysed (% T) unless stated otherwise. Cell debris was electronically excluded from analysis before gating for viable, CD3+/CD4+/CD45RO+/CD5+ cells which were ultimately analyzed for TAG-72 expression.
Figure 1B:
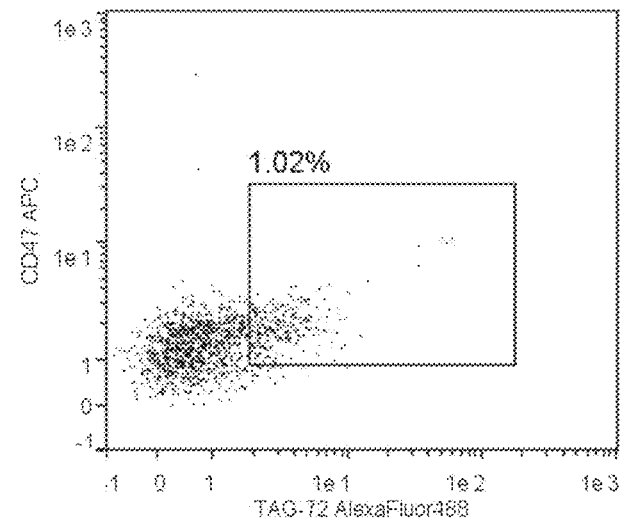
Figure 1C:
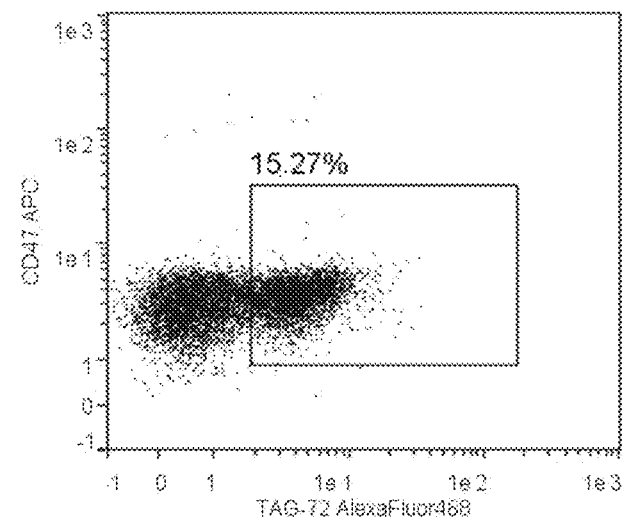
Figure 1D:
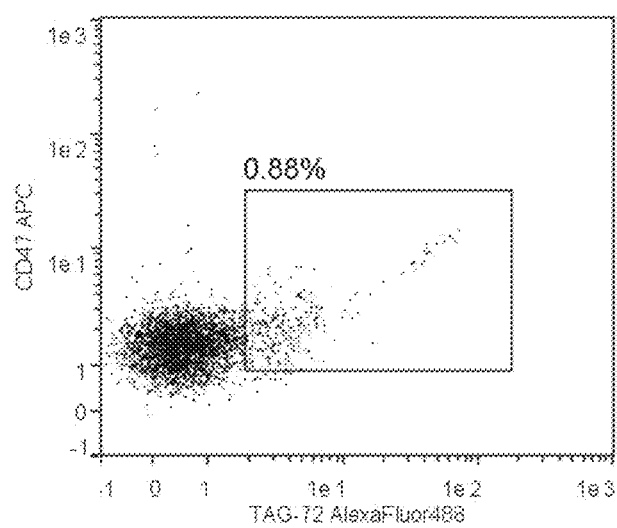
Figure 1E:
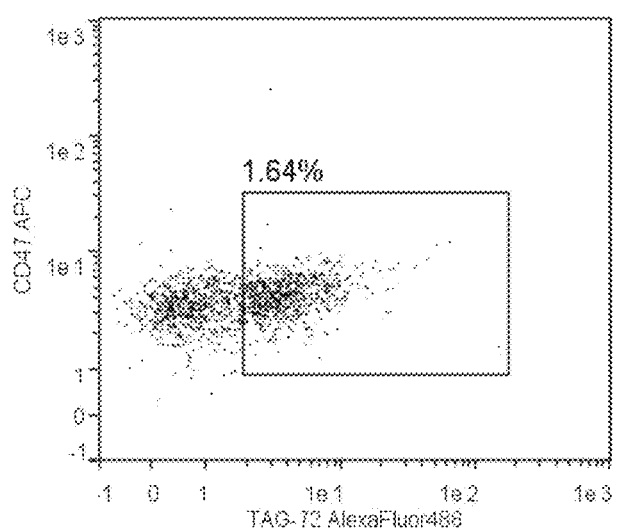
Figure 1F:
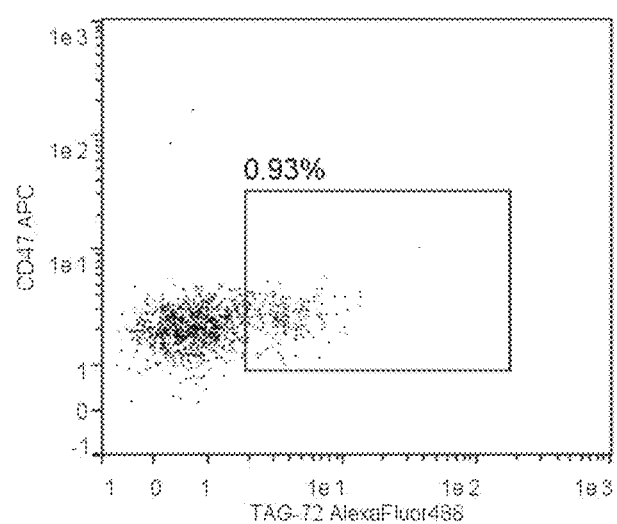
Figure 1G:
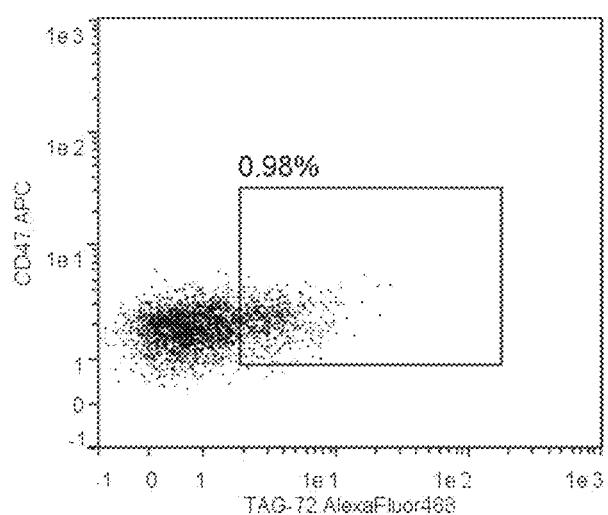
Figure 1H:
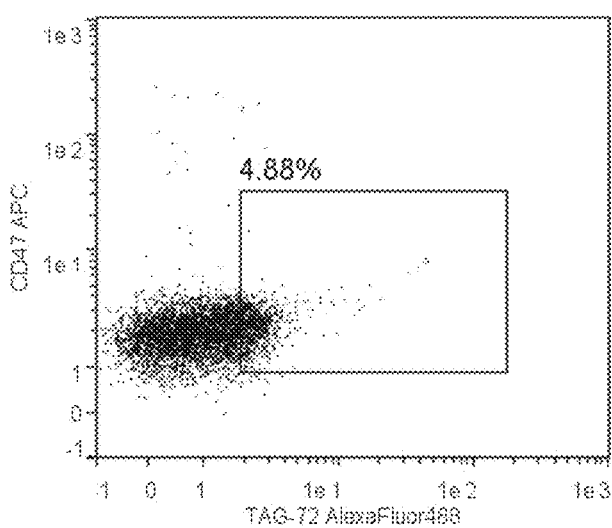
Figure 1I:
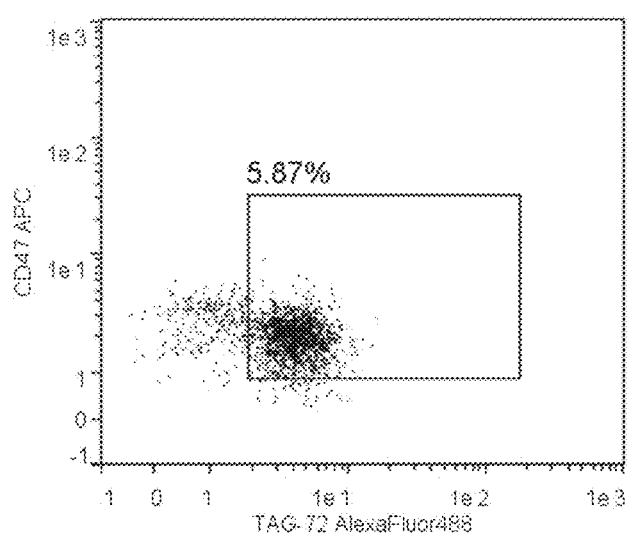
Figure 1J:
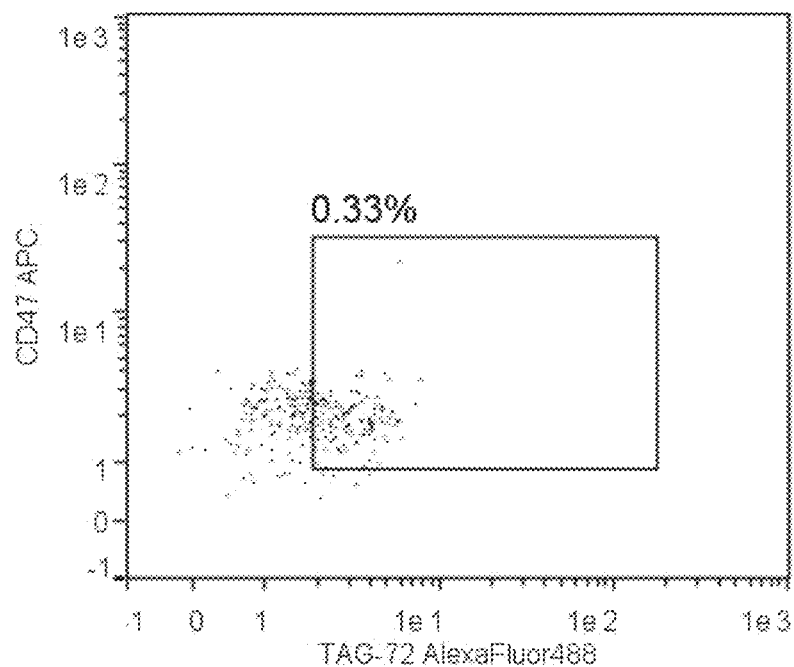
Figure 1K:
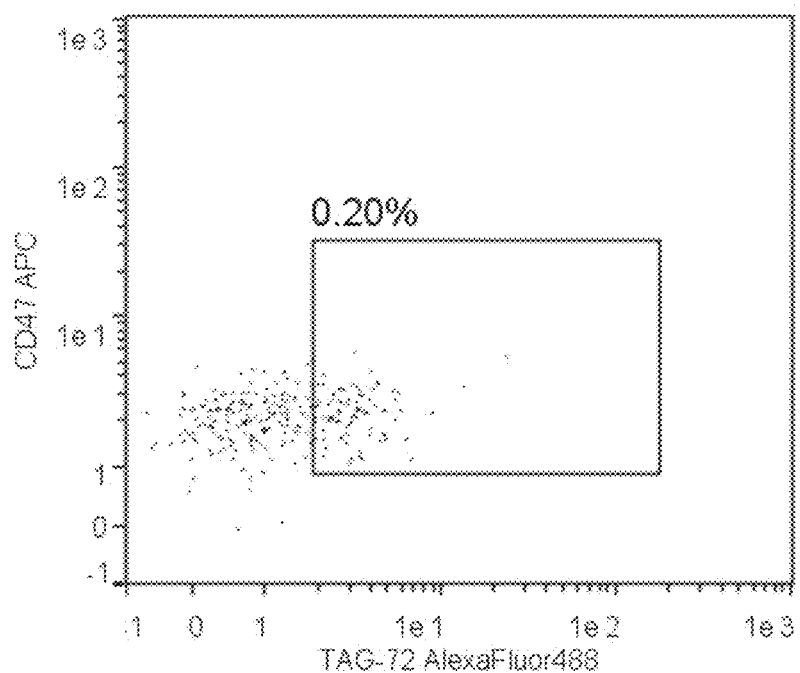
Figure 1L:
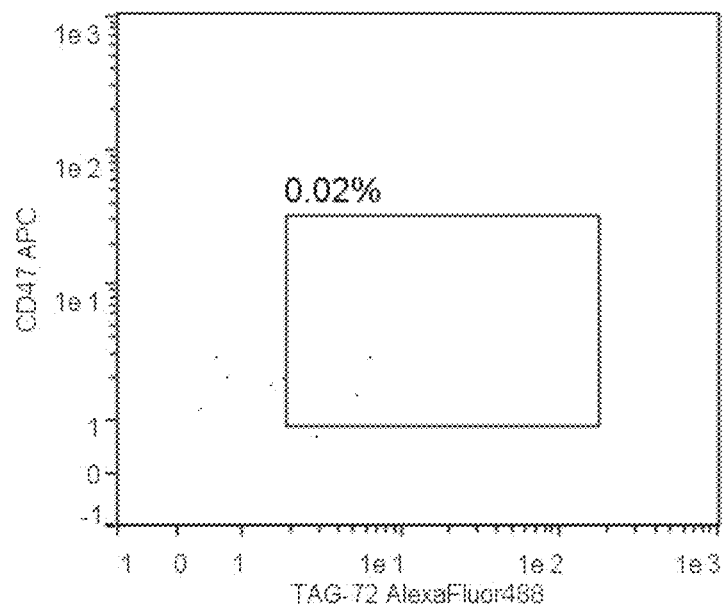
Figure 1M:
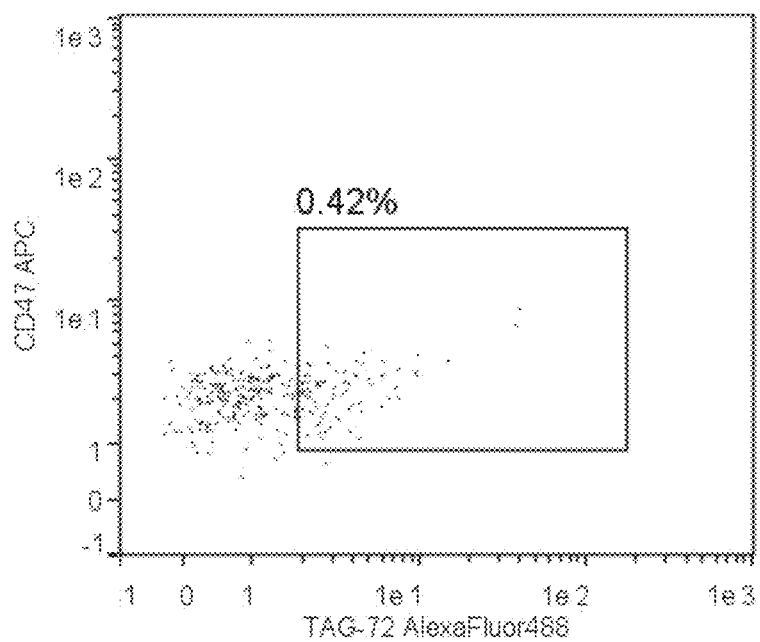
Figure 1N:
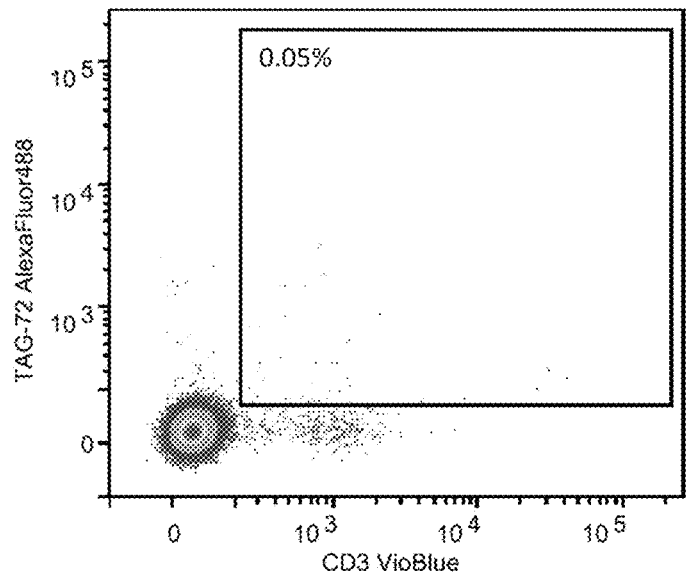
FIGS. 1N-1V. T-ALL and B-ALL samples do not express the tumor-associated antigen TAG-72, as demonstrated by flow cytometry. TAG-72 levels did not exceed baseline in T-ALL (N-R) or B-ALL (S-V) patient samples. Figures represent population frequency as a percent of viable events analyzed unless stated otherwise. Cell debris was electronically excluded from analysis before gating for single, viable cells which were ultimately analyzed for the co-expression of TAG-72 with either CD3 (T-ALL) or CD19 (B-ALL).
Figure 1O:
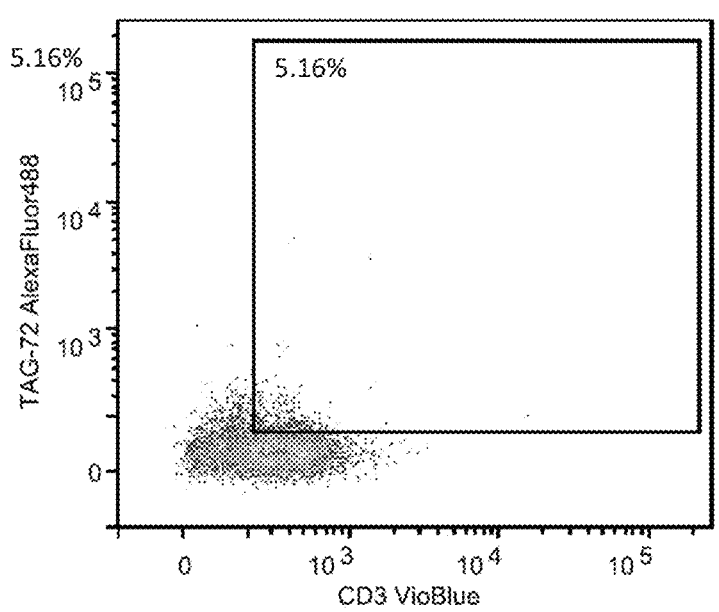
Figure 1P:
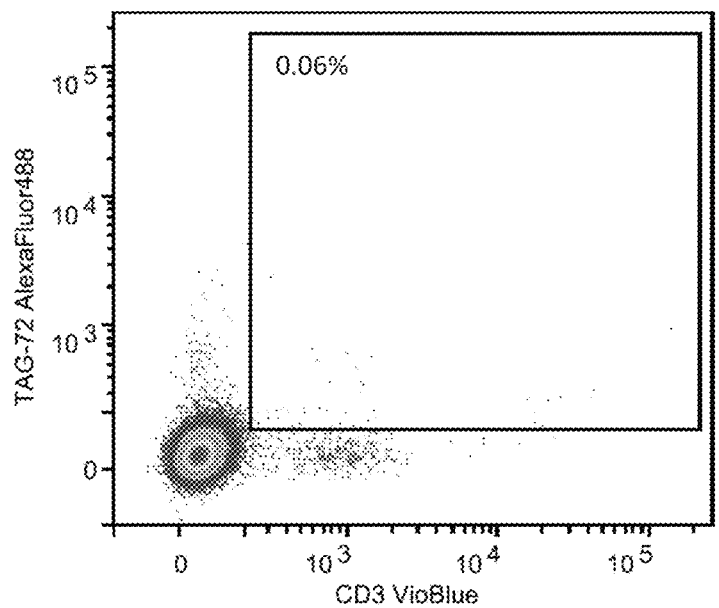
Figure 1Q:
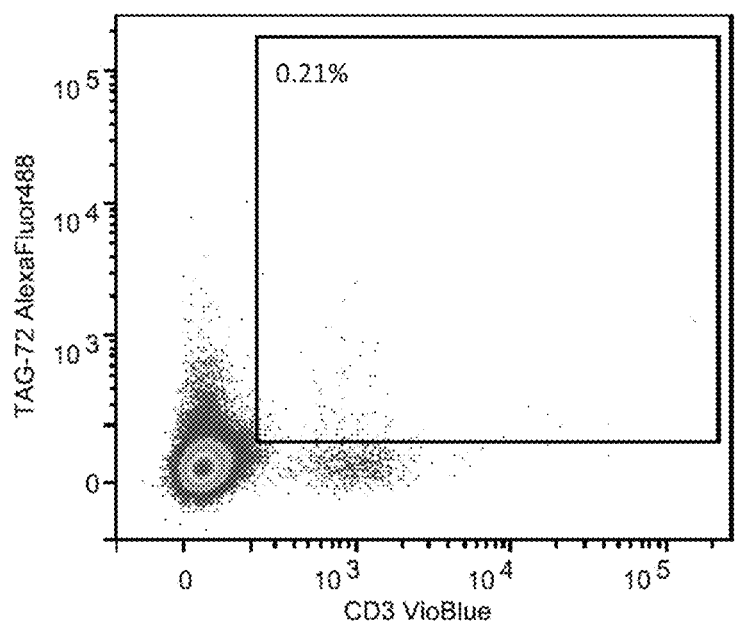
Figure 1R:
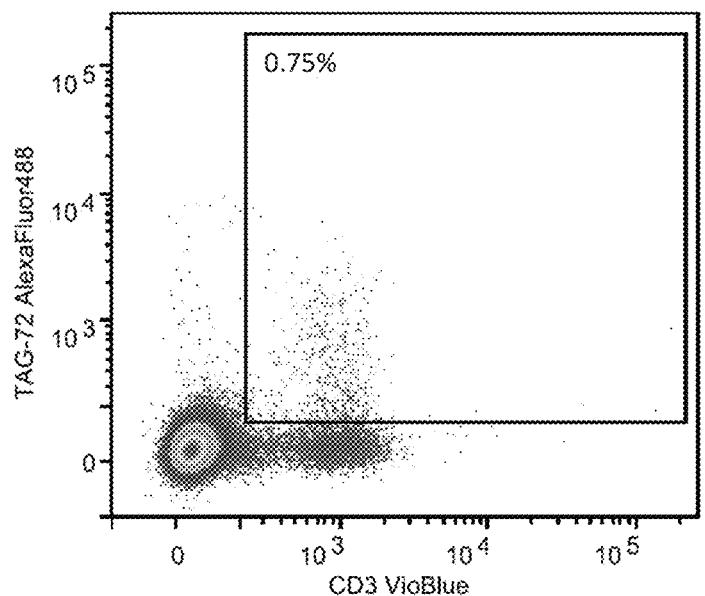
Figure 1S:
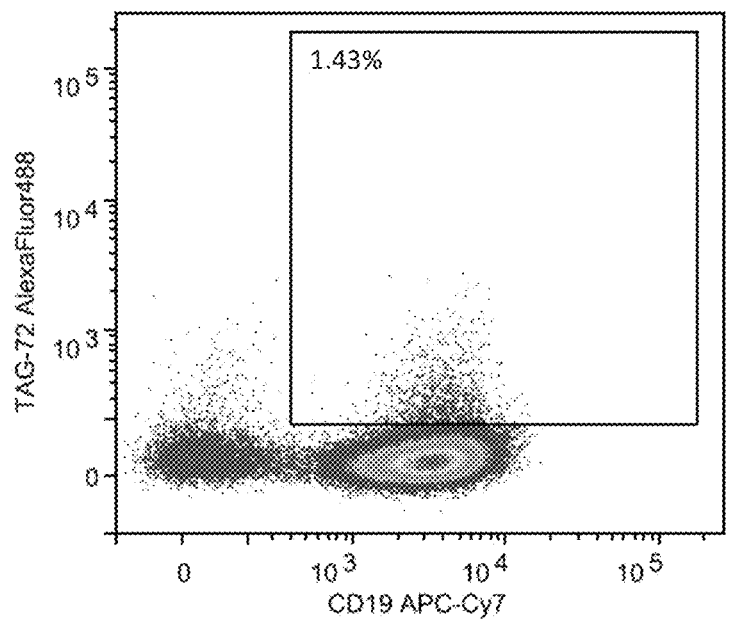
Figure 1T:
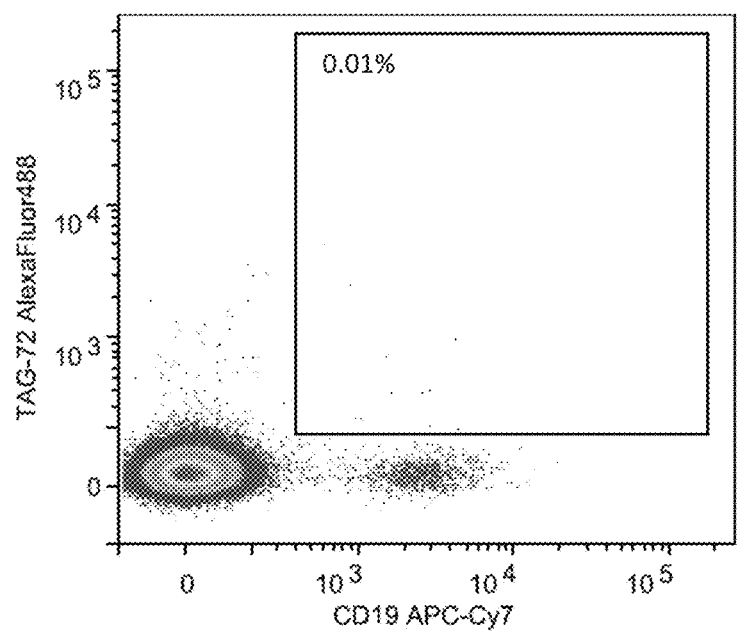
Figure 1U:
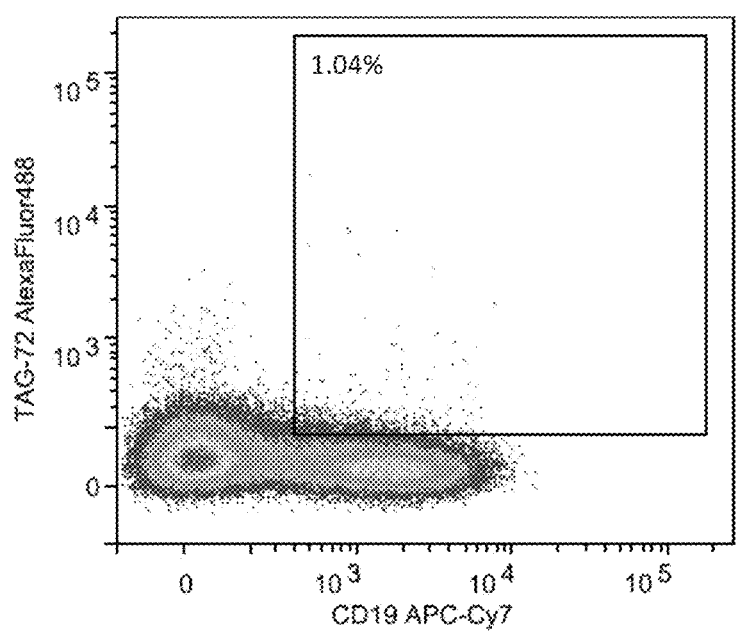
Figure 1V:
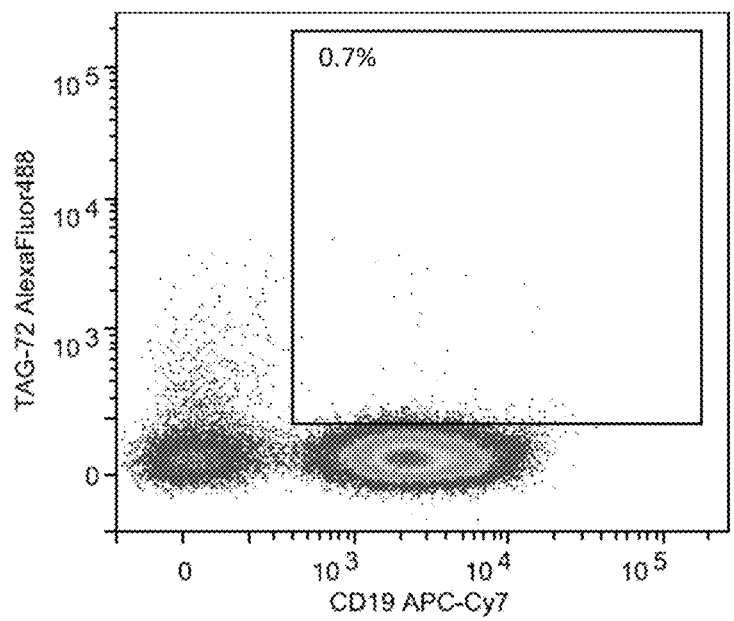

It has been identified in accordance with the present invention that TAG-72 is expressed by cells in TCL, in particular CTCL sub-types such as Sezary Syndrome (SS) and mycosis fungoides (MF). It has been demonstrated herein that CAR-T cells targeting TAG-72 specifically kill TCL T cells in vitro, and that an TAG-72 antibody-drug conjugate substantially reduces the percentage of TAG-72+ cells in PBMCs from SS patients. Accordingly, disclosed herein are methods of treating TCLs such as SS and MF by administration of TAG-72 targeting agents.

TCL, CTCL and SS

The therapeutic methods disclosed herein are effective for treating all forms of TCLs, including CTCL sub-types, including, for example, SS, anaplastic large-cell lymphoma, erythrodermic mycosis fungoides, and follicular trophic mycosis fungoides.

TCL is a class of non-Hodgkin's lymphoma that is caused by a T cell mutation. Peripheral T cell lymphomas (PTCLs) originate away from the thymus. One particular form, cutaneous T-cell lymphoma (CTCL), refers to T-cell lymphomas that involve the skin. The cancerous T cells form cutaneous lesions before spreading to other parts of the body. CTCL can also involve the blood, the lymph nodes, and other internal organs. Symptoms can include dry skin, itching, a red rash, and enlarged lymph nodes. Most patients with CTCL experience only skin symptoms without serious complications; however, approximately 10 percent of those who progress to later stages develop serious complications.

The two most common types of CTCLs are mycosis fungoides and SS. Mycosis fungoides is the most common type of CTCL, with skin symptoms that can appear as patches, plaques, or tumors. SS is an advanced, variant form of mycosis fungoides, and is characterized by the presence of lymphoma cells in the blood (T cells characterised by a range of surface markers and carrying pathological levels of mucopolysaccharides). The primary manifestation of SS is in the skin, with extensive thin, red, itchy rashes typically covering over 80 percent of the body.

TAG-72

TAG-72 was initially identified as being reactive to monoclonal antibody B72.3, which had been extensively characterized for its range of reactivity to a variety of carcinomas versus normal tissues (Sheer et al., *Cancer Res* 48, 6811-6818, 1988). Further characterization has established TAG-72 as a mucin-associated truncated 0-glycan containing a sialic acid α-2,6 linked to GalNAc α-O-Ser/Thr, also known as sialyl-Tn antigen (Munckley, Int. J. Mol. Sci. 2016, 17, 275).

Agent Targeting TAG-72

By "agent targeting TAG-72", it is meant an agent that specifically binds to TAG-72 expressed on the surface of cancerous cells and leads to killing of the cancerous cells.

Antigen Recognition Moiety

The agents targeting TAG-72 disclosed herein include an antigen recognition moiety that specifically recognizes and binds TAG-72. Specificity of a TAG-72 recognition moiety can be reflected by a dissociation constant ($K_D$) that is at least in the micromolar range, preferably a $K_D$ that is in the nanomolar or the picomolar range.

In various embodiments, antigen recognition moieties are composed of antigen-binding fragments of an antibody that specifically binds TAG-72.

The term "antibody" as used herein includes monoclonal antibodies of any isotype such as IgG, IgM, IgA, IgD and IgE, polyclonal antibodies, chimeric antibodies, humanized antibodies, multispecific antibodies, and single-chain antibodies. A typical IgG antibody is composed of two identical heavy chains and two identical light chains that are joined by disulfide bonds. Each of the heavy and light chains contains a constant region and a variable region. Each variable region contains three "complementarity-determining regions" ("CDRs") that are primarily responsible for binding an epitope of an antigen. The term "$V_H$" refers to the variable region of an immunoglobulin heavy chain of an antibody, including the heavy chain of an Fv, scFv, dsFv, Fab, Fab' or F(ab')2 fragment. The term "$V_L$" refers to the variable region of an immunoglobulin light chain of an antibody, including the light chain of an Fv, scFv, dsFv, Fab, Fab' or F(ab')2 fragment. The more highly conserved portions of the variable regions are referred to as the "framework regions".

The term "chimeric antibody", as used herein, refers to an antibody in which the constant regions or a portion thereof and the variable regions are of different origins. For example, DNA segments encoding the variable regions of the heavy and light chains of a murine monoclonal antibody can be cloned and joined to DNA segments encoding the constant regions of the heavy and light chains of a human immunoglobulin, respectively, to produce murine-human chimeric immunoglobulin-encoding genes.

The term "humanized antibody", as used herein, refers to an antibody derived from a non-human immunoglobulin wherein certain amino acids of the non-human immunoglobulin have been replaced by amino acids of human immunoglobulins. The goal of humanization is to reduce the immunogenicity of a xenogenic antibody, such as a murine antibody, for introduction into a human recipient, while maintaining the full antigen binding specificity of the antibody. Humanization of non-human antibodies can be made using technologies well known in the art, including for example, CDR-grafting (grafting the complementarity determining regions of a non-human immunoglobulin into a human immunoglobulin framework domain; see, e.g., WO 92/22653, EP 0 239 400, WO 91/09967, U.S. Pat. Nos. 5,530,101, and 5,585,089), resurfacing (altering the non-CDR surfaces of antibody variable regions based on a combination of molecular modeling, statistical analysis and mutagenesis in order to resemble the surfaces of known human antibodies; see, e.g., EP 0 592 106, EP 0 519 596), and chain shuffling (U.S. Pat. No. 5,565,332).

The term "multispecific antibody" refer to antibodies capable of selectively binding, or having specificities to, two or more epitopes—either on two different molecules (e.g., antigens) or on the same molecule (e.g., on the same antigen). For example, an example of a multispecific antibody is a bispecific antibody capable of selectively binding two or more epitopes. Generation of bispecific antibodies is well documented in the art.

The term "antibody fragments", as used herein, include any portion of an antibody that retains the ability to bind to the epitope recognized by the full length antibody. Examples of antibody fragments include, but are not limited to, Fab, Fab' and F(ab')$_2$, Fd, single-chain Fvs (scFv), disulfide-linked Fvs (dsFv), and fragments comprising either a $V_L$ or VH region. Antigen-binding fragments of antibodies can comprise the variable region(s) alone or in combination with a portion of the hinge region, CH1, CH2, CH3, or a combination thereof. Preferably, the antibody fragments contain all six CDRs of the whole antibody, although fragments containing fewer than all six CDRs may also be functional.

"Single-chain FVs" ("scFvs") are antigen-binding fragments that contain the heavy chain variable region ($V_H$) of an antibody linked to the light chain variable region ($V_L$) of the antibody in a single polypeptide, but lack some or all of the constant domains of the antibody. The linkage between the $V_H$ and $V_L$ can be achieved through a short, flexible peptide selected to assure that the proper three-dimensional folding of the $V_L$ and $V_H$ regions occurs to maintain the target molecule binding-specificity of the whole antibody from which the scFv is derived. scFvs lack some or all of the constant domains of antibodies.

For the antigen recognition moiety of TAG-72 targeting agents of this disclosure, antibodies directed to TAG-72 are available in the art and can also be made using known techniques. Multiple second generation murine monoclonal antibodies were developed against TAG-72, including CC49 and CC112, among many others (Molinolo et al., *Cancer Res* 1990; 50(4): 1291-1298). Such monoclonal antibodies, and chimeric or humanized forms thereof, can be used to provide antigen recognition moieties of agents targeting TAG-72. A humanized TAG-72 antibody (huCC49) derived from the mouse CC49 antibody (muCC49) has been described in U.S. Pat. No. 8,835,167 B2.

In specific embodiments, the antigen recognition moiety comprises the 6 CDRs of the mouse monoclonal antibody CC49.

In some embodiments, the antigen recognition moiety comprises 6 CDRs having amino acid sequences having at least 95%, 96%, 97%, 98%, 99% or greater identity to SEQ ID NOS: 12-17. In specific embodiments, the antigen recognition moiety comprises 6 CDRs having the amino acid sequences as set forth in SEQ ID NOS: 12-17.

In some embodiments, the antigen recognition moiety comprises a heavy chain variable region (VH) which comprises an amino acid sequence having at least 95%, 96%, 97%, 98%, 99% or greater identity to the amino acid sequences from amino acids Q1 to S115 of SEQ ID NO: 2.

In some embodiments, the antigen recognition moiety comprises a light chain variable region (VL) which comprises an amino acid sequence having at least 95%, 96%, 97%, 98%, 99% or greater identity to the amino acid sequences from amino acids D131-R244 of SEQ ID NO: 2.

In some embodiments, the antigen recognition moiety comprises (i) a heavy chain variable region (VH) which comprises an amino acid sequence having at least 95%, 96%, 97%, 98%, 99% or greater identity to the amino acid sequences from amino acids Q1 to S115 of SEQ ID NO: 2; (ii) a light chain variable region (VL) which comprises an amino acid sequence having at least 95%, 96%, 97%, 98%, 99% or greater identity to the amino acid sequences from amino acids D131-R244 of SEQ ID NO: 2; and wherein the VH and VL regions comprise 6 CDRs having the amino acid sequences as set forth in SEQ ID NOS: 12-17.

In a specific embodiment, the antigen recognition moiety comprises a heavy chain variable region (VH) composed of amino acids Q1 to S115 of SEQ ID NO: 2 and a light chain variable region (VL) composed of amino acids D131-R244 of SEQ ID NO: 2.

In accordance with this disclosure, the agents targeting TAG-72 achieve killing of TAG-72 expressing cancerous cells after binding of the agents to such cancerous cells. The killing is achieved in various ways depending on the form of a TAG-72 targeting agent which can include drug conjugated antibodies or antigen-binding fragments, antibodies with enhanced cytotoxic effector functions such as antibody-dependent cell mediated cytotoxicity (ADCC), bispecific antibodies, and cells expressing a chimeric antigen receptor (CAR).

Drug-Conjugated Antibodies or Antigen-Binding Fragments

In some embodiments, the agent is an anti-TAG-72 antibody or antigen-binding fragment thereof conjugated, e.g., covalent attached, to a cytotoxic agent.

The cytotoxic agent used for conjugation to an anti-TAG-72 antibody or antigen-binding fragment may be any compound that results in the death of a cell, or induces cell death, or in some manner decreases cell viability. In some embodiments, the cytotoxic agent is a small molecule compound, including particularly small molecule compounds that have anti-cancer properties. The term "small molecule compound" includes low molecular weight compounds (less than 1500, 1200, 1000, 800 or even 600 dalton) that have simple and well define chemical structure. Examples include a taxoid, a maytansinoid (such as DM1 or DM4), a tomaymycin derivative, a leptomycin derivative, a duocarmycin (e.g., CC-1065) or analog thereof, Aurostatins and pyrrolobenzodiazepine dimer. Additional drugs such as methotrexate, daunorubicin, doxorubicin, vincristine, vinblastine, melphalan, mitomycin C, chlorambucil, calicheamicin, tubulysin and tubulysin analogs, dolastatin and dolastatin analogs, are also suitable for use herein in the preparation of conjugates.

A cytotoxic agent can be covalently attached, directly or via a linker, to the antibody or antigen-binding fragment thereof. Suitable linkers are well known in the art and include disulfide groups, thioether groups, acid labile groups, photolabile groups, peptidase labile groups and esterase labile groups. For example, conjugates can be constructed using a disulfide exchange reaction or by forming a thioether bond between the antibody and a small molecule compound. The small molecules can also be linked to the antibody molecules through an intermediary carrier molecule such as serum albumin.

TAG-72 Specific Antibodies with Improved ADCC Activity

In some embodiments, a TAG-72 targeting agent is an anti TAG-72 antibody with an enhanced ability to mediate cellular cytotoxic effector functions such as antibody-dependent cell-mediated cytotoxicity (ADCC). Such antibodies may be obtained by making one or more amino acid substitutions in the constant framework regions of an antibody, thus altering the interaction of the antibody with the Fc receptors on cytotoxic effector cells. See, e.g., Lazar et al. (*Proc. Natl. Acad. Sci. USA.* 103(11): 4005-4010, 2006).

In other embodiments, a TAG-72 targeting agent is a bispecific antibody that is specific for TAG-72 and a receptor present on cytotoxic effector cells (e.g., CD16, which is present on NK cells). Such bispecific antibodies can bring cytotoxic effector cells to the vicinity of TAG-72 expressing cancer cells, resulting in more effective killing of the cancerous cells by the cytotoxic effector cells. Bispecific antibodies directed to a tumor antigen and a NK cell receptor have been described (see, e.g., Schmohl et al., *Mol. Ther.* 24(7):1312-22, 2016). The VH and VL regions of a bispecific antibody that confer specificity to TAG-72 can be any of the VH or VL regions specific for TAG-72 described herein above.

CAR-Expressing Cells

In other embodiments, the agent is a cell expressing a chimeric antigen receptor (CAR) comprising an antigen recognition moiety specific for TAG-72.

The term "chimeric antigen receptor" (also known as an "artificial T cell receptor", "chimeric T cell receptor" and "chimeric immunoreceptors") refers to engineered receptors which graft an antigen binding moiety onto an immune effector cell. These receptors are used herein to graft the TAG-72 specificity of a monoclonal antibody onto a T cell or an NK cell. Generally speaking, CARs are composed of an antigen recognition moiety specific for TAG-72, a transmembrane domain, and an intracellular/cytoplasmic signaling domain (also referred to as an endodomain) of a receptor natively expressed on an immune effector cell, operably linked to each other such that when immune effector cells express such a CAR, they recognize and kill target cells that express TAG-72. By "operably linked" is meant that the individual domains are linked to each other such that upon binding of the antigen recognition moiety to TAG-72, a signal is induced via the intracellular signaling domain to activate the cell that expresses the CAR (e.g., a T cell or an NK cell) and enable its effector functions to be activated.

Antigen-Recognition Moiety—The antigen-recognition moiety of CARs is an extracellular portion of the receptor which recognizes and binds to an epitope of the target antigen (i.e., TAG-72 herein). The antigen-recognition moiety is usually a scFv, formed by having the heavy and light variable regions of an anti-TAG-72 monoclonal antibody fused to each other by a flexible linker. In some embodiments, the CAR is engineered to have a signal peptide at the N-terminal end of the antigen recognition moiety. Any eukaryotic signal peptide sequence may be used. Generally, a signal peptide natively attached to the amino-terminal is used (e.g., in a scFv with orientation light chain-linker-heavy chain, the native signal of the light-chain is used).

Intracellular Signaling Domain (or "endodomain")—The antigen recognition moiety is operably linked to an intracellular signaling domain which, upon antigen recognition and binding, transmits the signal to the intracellular part of the cell (a T cell or an NK cell) to enable its activation and effector mechanism induction. The antigen recognition moiety may be operably linked to one of the subunits of the natural TCR, or to an artificial receptor such as a chimeric antigen receptor (CAR). T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences). Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use include those derived from TCR zeta, FcR gamma, FcR beta, CD3 gamma, CD3 delta, CD3 epsilon, CD5, CD22, CD79a, CD79b, and CD66d. In some embodiments, the intracellular signaling domain of CARs disclosed herein comprises a cytoplasmic signaling sequence from CD3-zeta. In some embodiments, the intracellular signaling domain of CARs disclosed herein comprises the intracellular domain of CD3-zeta, or comprises a portion of the intracellular domain of CD3-zeta that contains the 3 ITAMs present in the native domain. While usually the entire intracellular signaling domain of native receptors can be employed, in many cases it is not necessary to use the entire domain. To the extent that a truncated portion of a native intracellular signaling domain is used, such truncated portion may be used in place of the intact domain as long as it transduces the effector function signal. In some instances, CD3-zeta may not provide a fully competent activation signal and additional co-stimulatory signaling is desirable. In some embodiments, the intracellular signaling domain of a CAR can comprise a CD3 zeta chain portion in combination with a costimulatory signaling region. The costimulatory signaling region can comprise the intracellular domain (or a functional portion thereof) of a costimulatory molecule. Examples of suitable costimulatory molecules include CD27, CD28, 4-1BB (CD137), OX40, CD30, CD40, PD-1, TIM3, ICOS, lymphocyte function-associated antigen-1 (LFA-1), CD2, CD7, LIGHT, NKG2C, B7-H3, and the like. The cytoplasmic signaling sequences (e.g., a CD3 zeta chain portion, and a costimulatory signaling region) within the intracellular signaling domain of a CAR may be linked to each other in a random or specified order. Optionally, a short oligo- or polypeptide linker, preferably between 2 and 10 amino acids in length may form the linkage. A glycine-serine doublet provides a particularly suitable linker. In one embodiment, the cytoplasmic domain is designed to comprise the signaling domain of CD3-zeta and the signaling domain of CD28.

Transmembrane Domain—The transmembrane domain of a CAR is generally a typical hydrophobic alpha helix that spans the membrane. In some embodiments, the transmembrane domain that is naturally associated with one of the domains in the CAR is used, e.g., the original molecule of the signaling endodomain which protrudes into the cell and transmits the desired signal. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. For example, transmembrane regions may be derived from the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of a CAR. A glycine-serine doublet provides a particularly suitable linker.

Spacer—The term "spacer" refers to any oligo- or polypeptide that links the transmembrane domain to either the extracellular domain or the cytoplasmic domain in the polypeptide chain. The spacer should be flexible enough to allow the antigen recognition moiety to orient in different directions to facilitate antigen recognition and binding. One simple form of a spacer region is the hinge region from IgG1. Alternatives include the $C_{H2}C_{H3}$ region of immunoglobulin and portions of CD3. For most scFv based CARs, an IgG1 hinge suffices. A spacer domain may comprise up to 300 amino acids, preferably 10 to 100 amino acids and most preferably 25 to 50 amino acids. In yet another example, one may modify the hinge region to change its length and thereby achieve additional functional benefits. For example, in a traditional CAR which comprises a CD8 or CD28 hinge, a single Cysteine (Cys) can be left in the hinge to stabilize dimerization on the T-cell surface. Thus two scFv are usually displayed (bivalent). In another example, one may substitute the Cys (for Ser) so that the stabilizing disulphide bond cannot form thereby preventing dimerization and hence premature activation. The Cys may also be removed entirely. Another design is to display just the VH domain on one CAR and VL domain on another, thus the Cys pairing will align the VH/VL to form a functional monovalent Fv, targeting the antigen of interest.

Figure 4A:
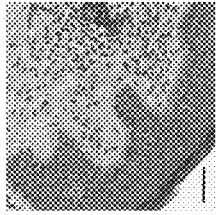
FIG. 4A. Skin biopsies from some CTCL patients show the presence of TAG-72 positive cells. Punch biopsies of lesion affected skin were obtained from 11 individuals diagnosed with SS, MF or anaplastic T cell lymphoma. Thin sections were prepared and stained by H&E and for expression of TAG-72 or CD3 using standard techniques. Representative regions of interest for each section and stain are shown in FIG. 4A, along with positive controls for TAG-72 and CD3 stained sections. Scale bar represents 50 um.
Figures 6A, 6B:
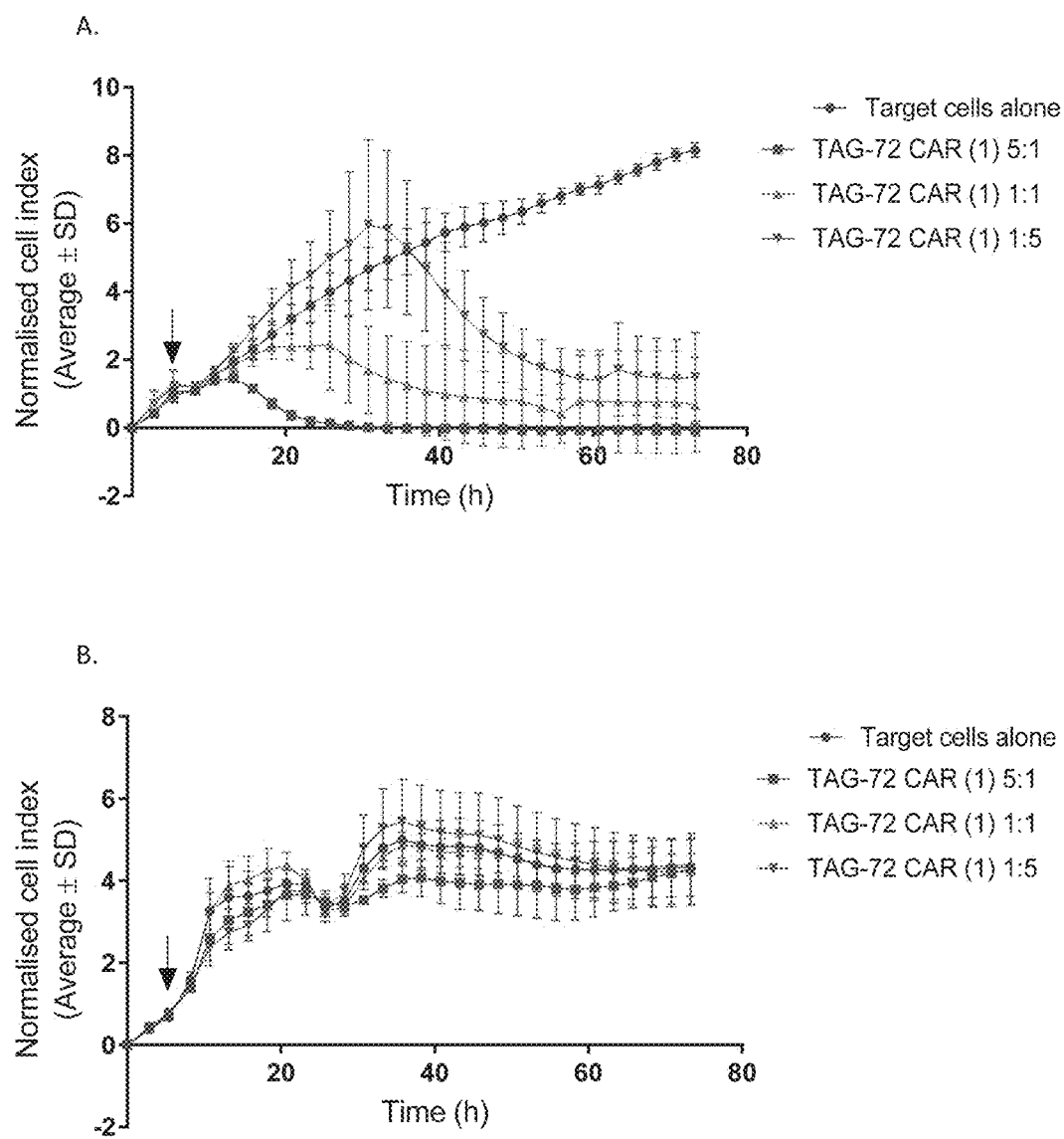
FIGS. 6A-6B. TAG-72 CAR (1) T cells mediate potent cell killing of TAG-72$^{hi}$ expressing target cancer cells (Ovcar 3) (A) but not TAG-72$^{-ve/low}$ cancer target cells (MESov) (B). Target cells were allowed to adhere to RTCA plates for 4 h before addition of effector cells (↓) at an E:T ratio of 5:1 (red), 1:1 (green) or 1:5 (purple). Cell impedance (represented here as normalised cell index) was monitored over 75 h. Target cell proliferation under normal growth conditions (blue) was also monitored throughout.
Figures 6C, 6D:
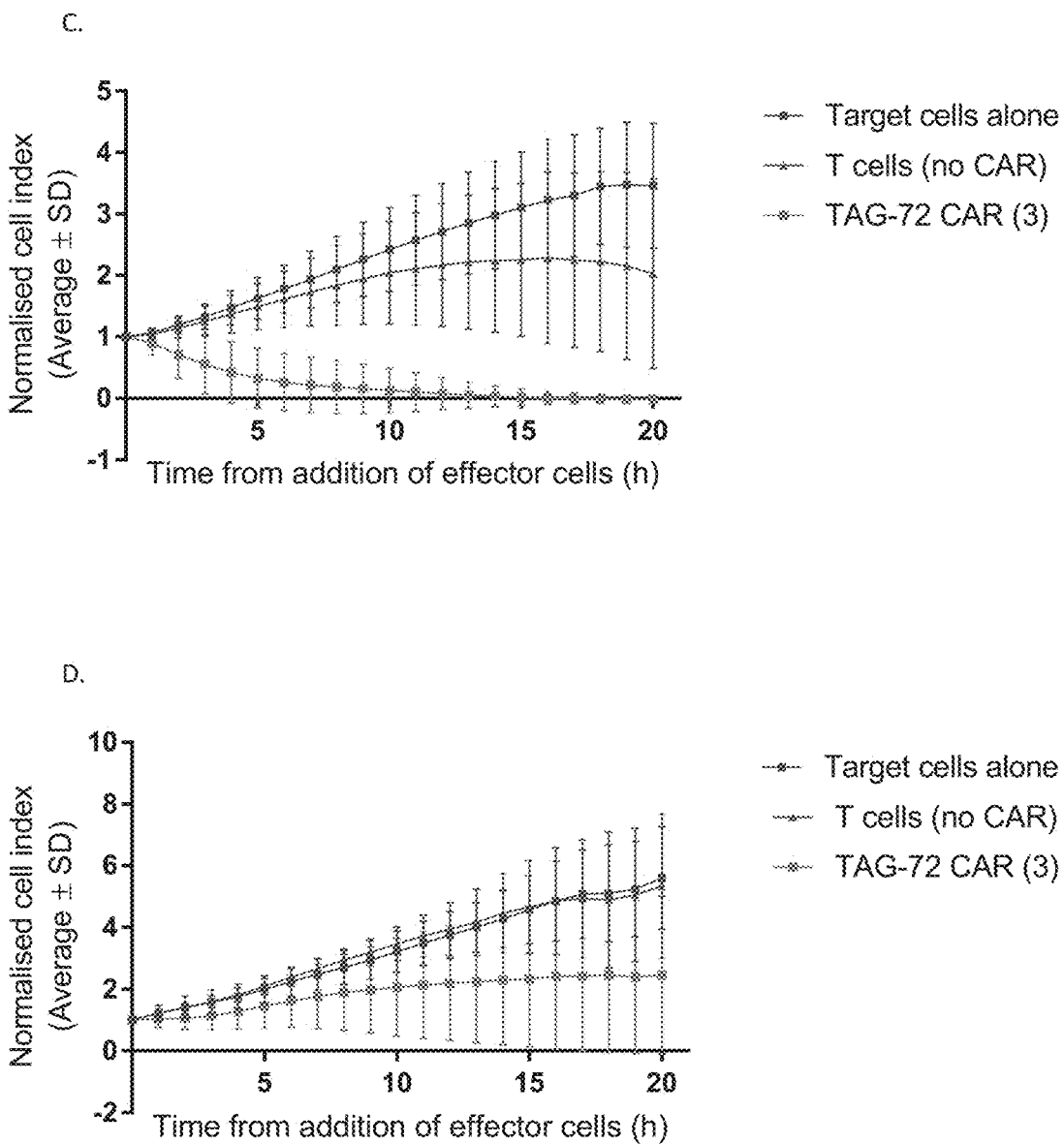
FIGS. 6C-6D. TAG-72 CAR (3) T cells media potent cell killing of TAG-72$^{hi}$ expressing target cells (Ovcar3) (C) but not TAG-72$^{-ve/low}$ cancer target cells (MESov) (D). Target cells were allowed to adhere to RTCA plates for 4-6 h before addition of NT T cells (red) or TAG-72 CAR (3) (green) at an E:T ratio of 5:1. Cell impedance (represented as normalised cell index) was monitored over 20 h. Target cell proliferation under normal growth conditions (blue) was also monitored throughout.
Figure 7A:
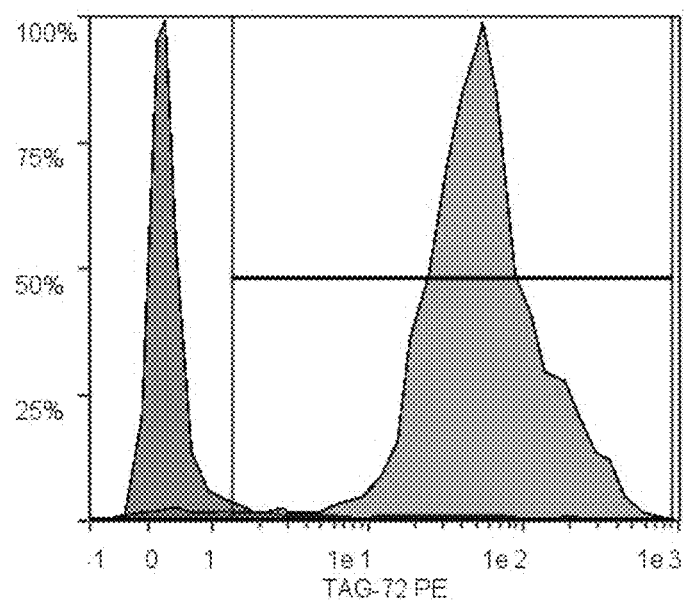
FIGS. 7A-7E. Jurkat cells can be killed by TAG-72-specific CAR-T cells in suspension cultures in vitro. The Jurkat cell line was characterized for TAG-72 expression (A; red) compared to isotype control (blue) before use in vitro. Jurkat cells were maintained under normal culture conditions (B), co-cultured with non-transduced T cells (C), TAG-72 CAR (1) T cells (D), or TAG-72 CAR (3) T cells (E) for 48 h, at which point analysis of viable TAG-72+ cells remaining within the cultures was determined by flow cytometry. Data are presented as percent of viable cells remaining in the culture that express TAG-72.
Figure 7B:
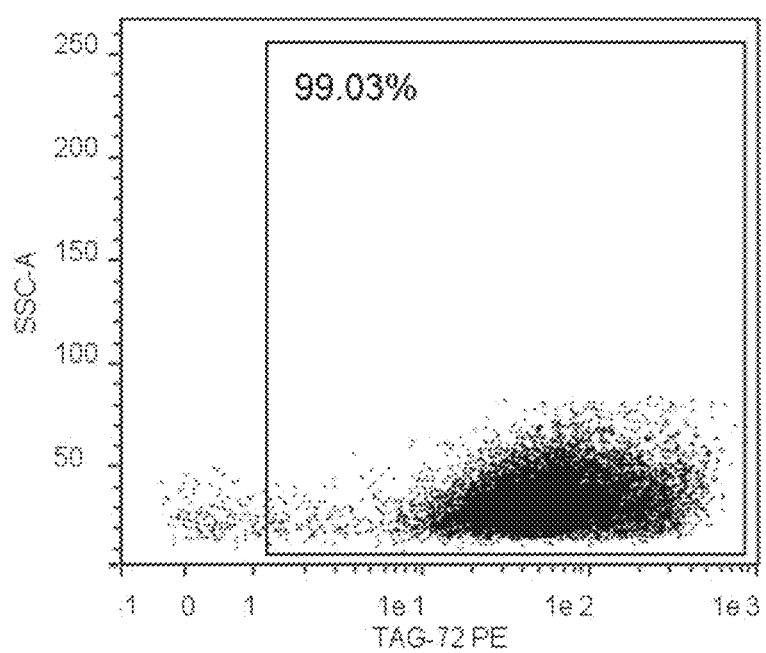
Figure 7C:
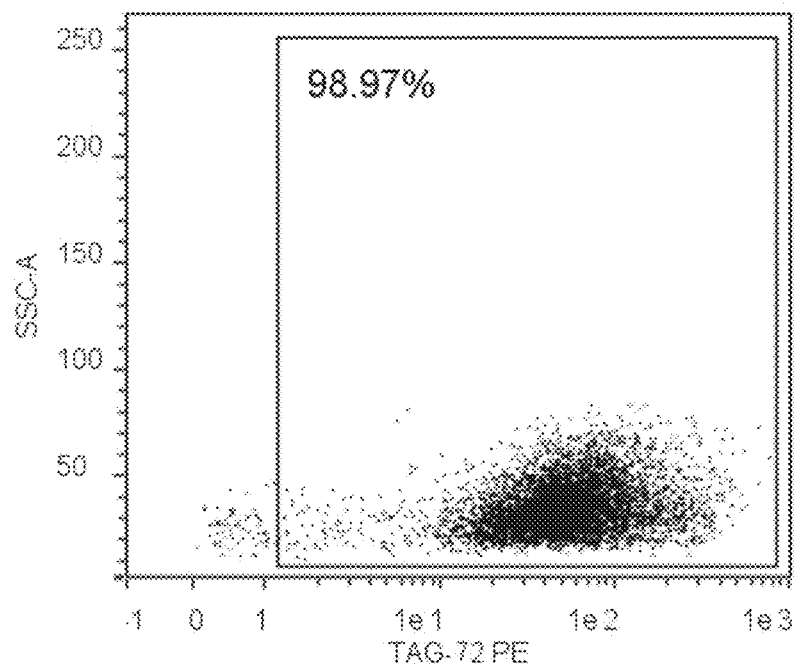
Figure 7D:
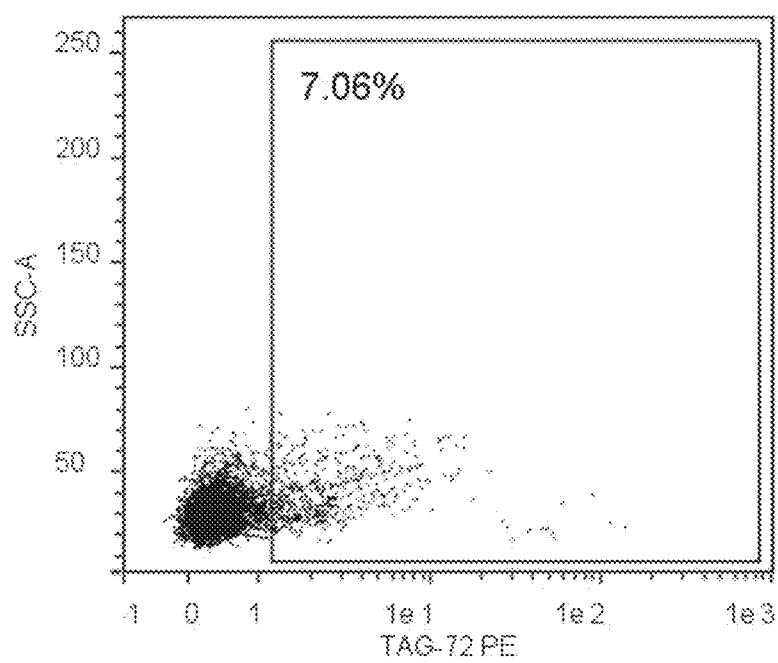
Figure 7E:
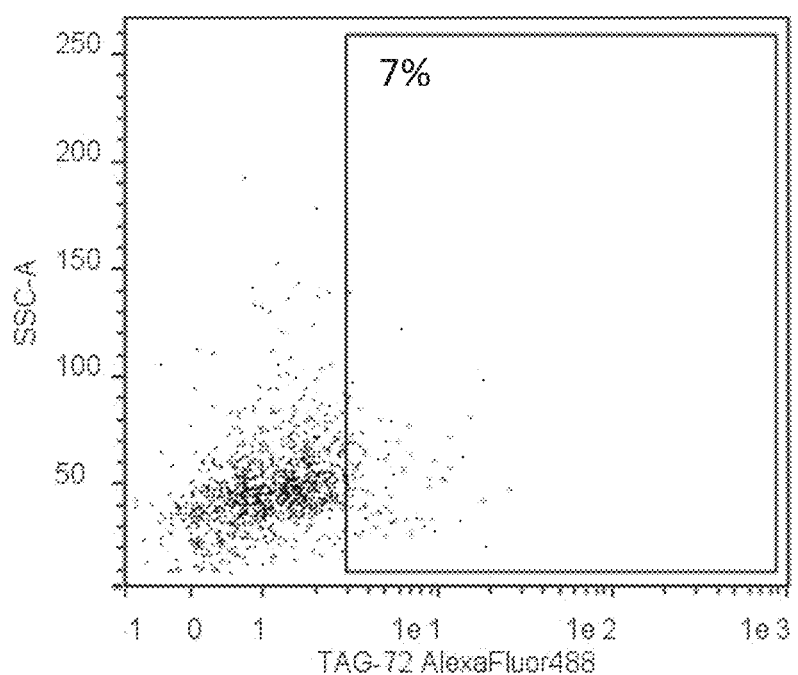
Figure 8A:
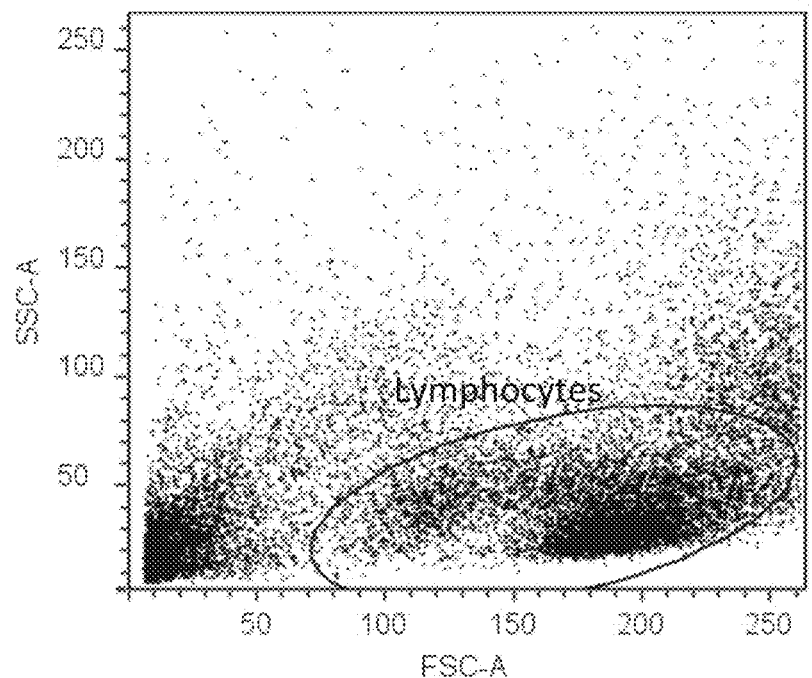
FIGS. 8A-8E. TAG-72+ cells within the lymphocyte population of SS patient PBMCs are reduced following 48 h exposure to TAG-72 CAR (1) T cells in vitro. Panels A-D represent results from a single SS patient. Exemplar gating strategy demonstrate debris was eliminated from analysis by gating for the lymphocyte population (A) before analyzing TAG-72 expression (B-D). E. Pooled data for 9 SS patients and 4 normal subjects from FIG. 2 demonstrates the persistence of TAG-72 expression on SS patient PBMCs in vitro when maintained under normal expansion conditions (blue). A slight reduction is observable in Patient/NT PBMC cultures (red) however this did not reach significance. The greatest change is observed when patient PBMCs are co-cultured with TAG-72 CAR (1) T cells (green). n.s.=non-significant; * represents p<0.05 in a t-test.
Figure 8B:
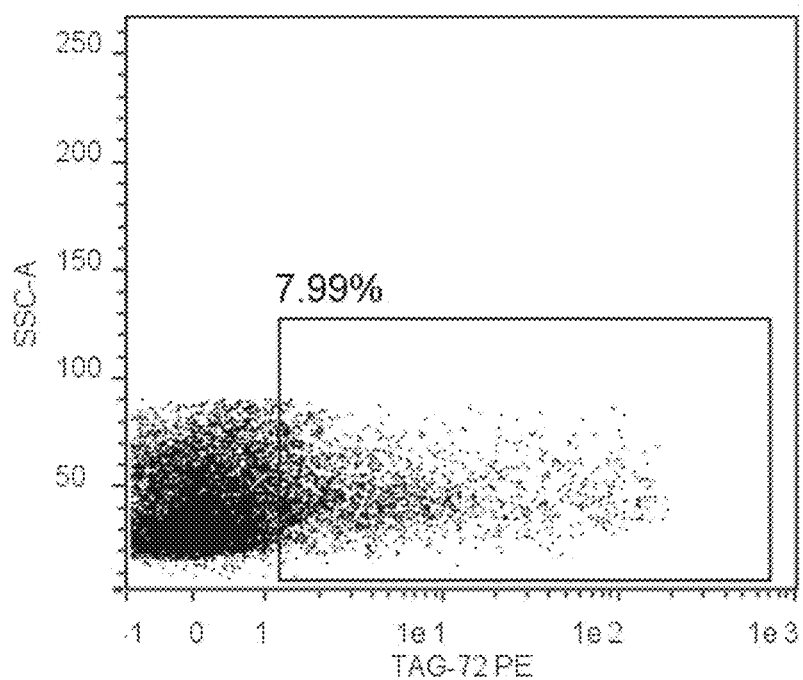
Figure 8C:
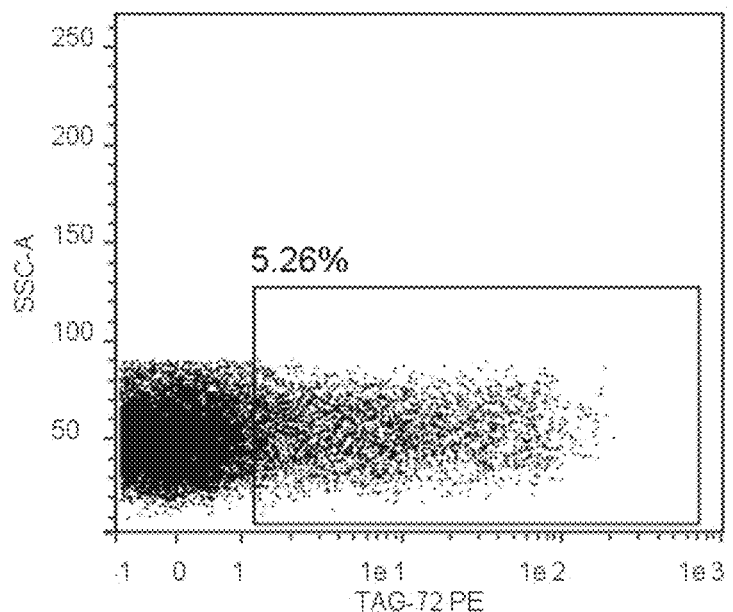
Figure 8D:
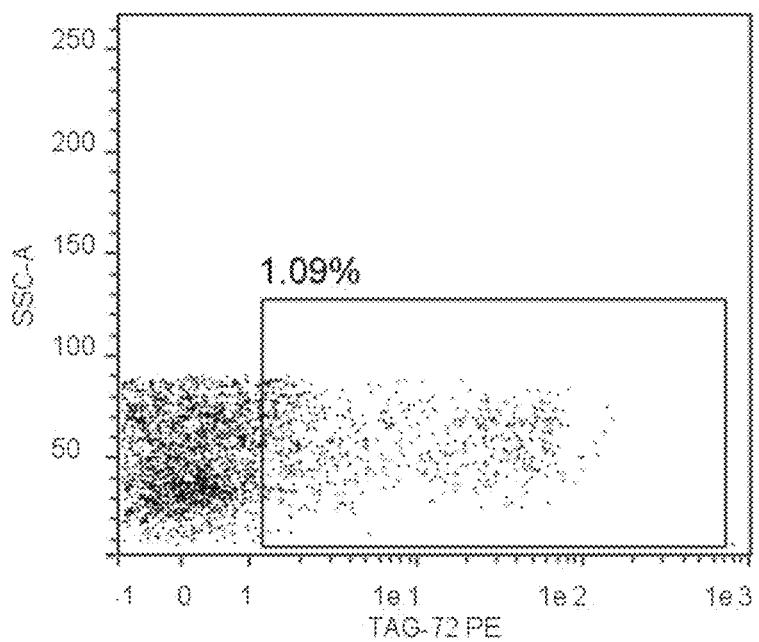
Figure 8E:
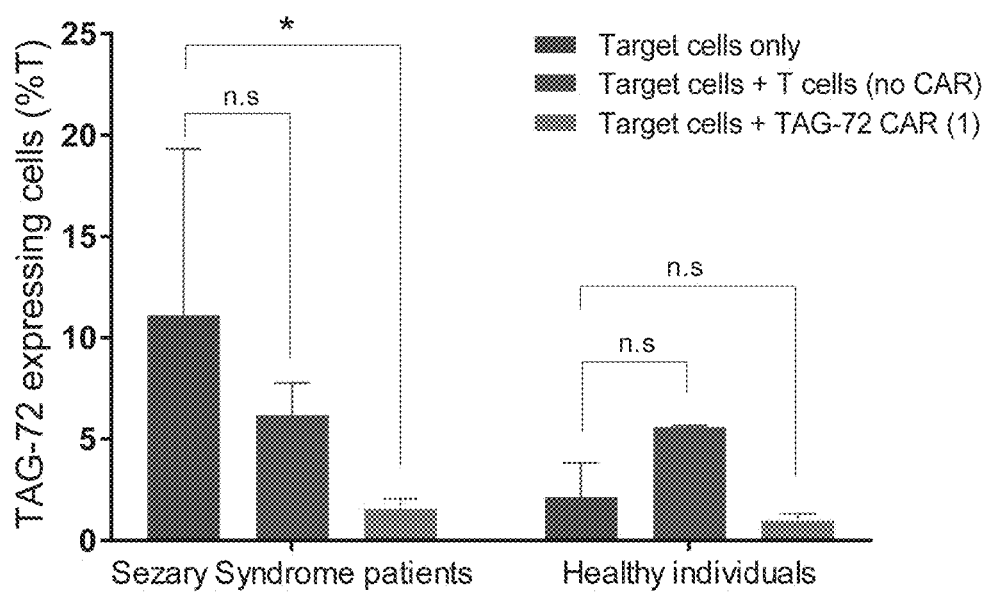
Figures 9A, 9B, 9C, 9D, 9E, 9F:
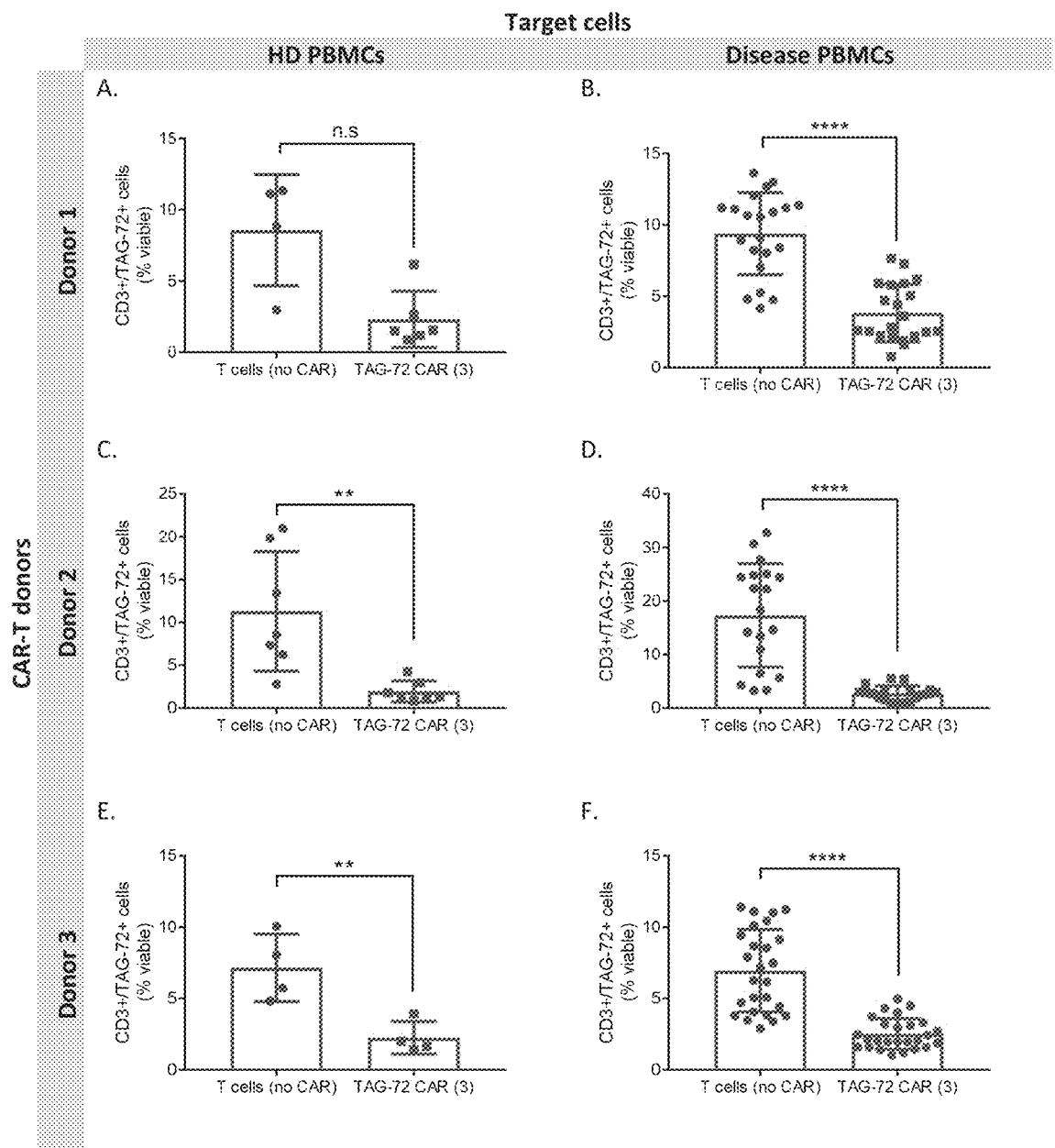
FIGS. 9A-9H. The frequency of CD3+/TAG-72+ in TCL PBMCs (subsequently designated Disease PBMCs) is significantly reduced following 24 h co-culture with TAG-72 CAR (3) T cells (red, B, D, F) compared to co-culture with non-transduced (NT) T cells (blue). Parallel co-cultures were performed with healthy donor (HD) PBMCs (A, C, E) where reduction of CD3/TAG-72+ cells was also observed in test conditions (red) albeit to a lesser degree. All cultures were prepared using an E:T of 5:1. Each target cell type (either disease or healthy subject or Jurkat cell line) was co-cultured with CAR-T cells generated from T cells isolated from at least two different donors.
Figure 9G:
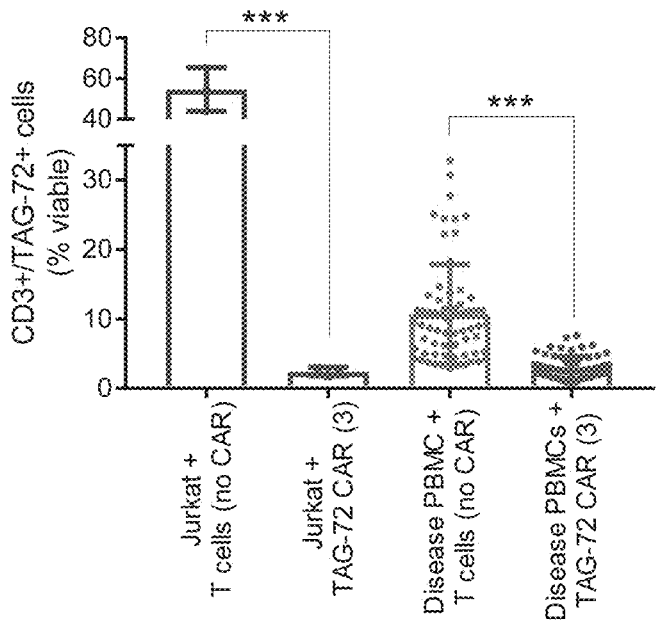
Figure 9H:
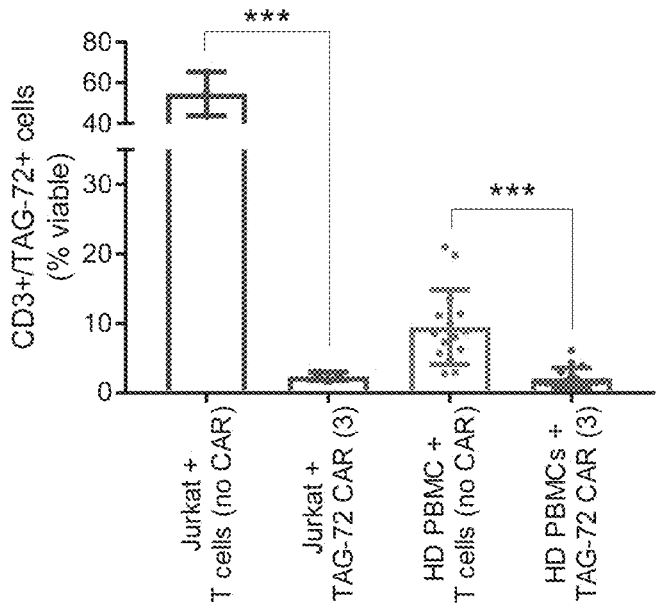
Figure 10A:
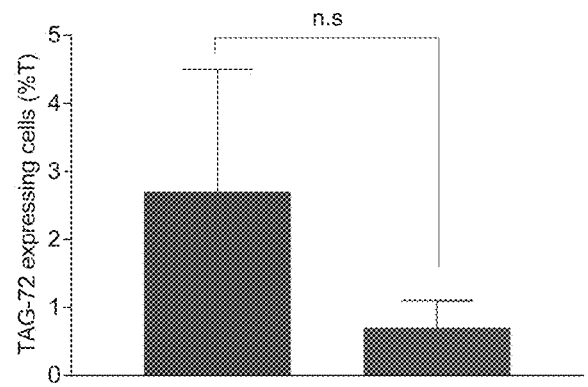
FIGS. 10A-10E. Killing of TAG-72+ cells using an anti-TAG-72 antibody-drug conjugate. Sezary Syndrome patient PBMCs expressing TAG-72 were diminished following exposure to the anti-TAG-72 antibody-drug conjugate CC49-DM1. Pooled data from four SS patient PBMCs exposed to CC49-DM1 over 48 h demonstrated a reduction in the total percent of cells expressing TAG-72 (A; red) compared to SS patient PBMCs maintained under normal culture conditions (blue). Exposure to this antibody-drug conjugate also reduced the frequency of TAG-72 expressing cells in Jurkat cultures (B) but not in healthy donor PBMCs (C). Exemplar FACS dotplots further demonstrate changes in this cell subpopulation in SS patient PBMCs in the absence (D) and presence (E) of antibody-drug conjugate.
Figure 10B:
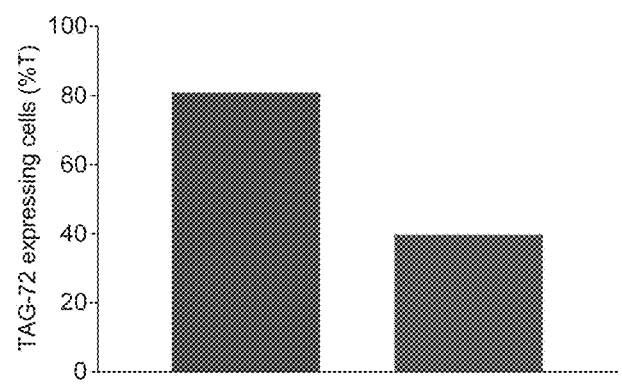
Figure 10C:
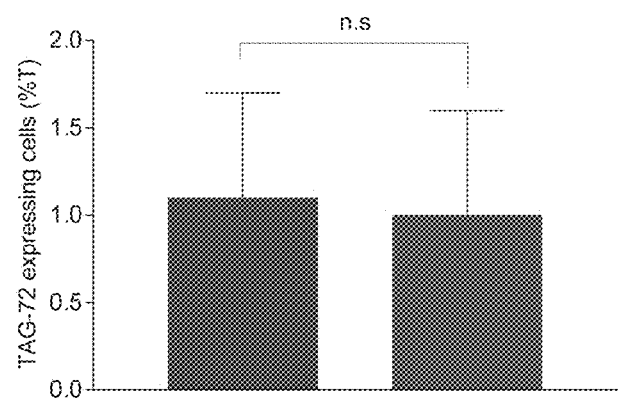
Figure 10D:
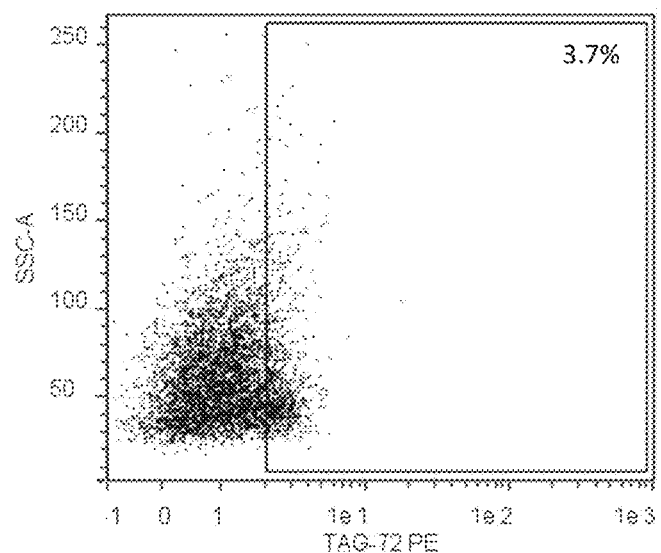
Figure 10E:
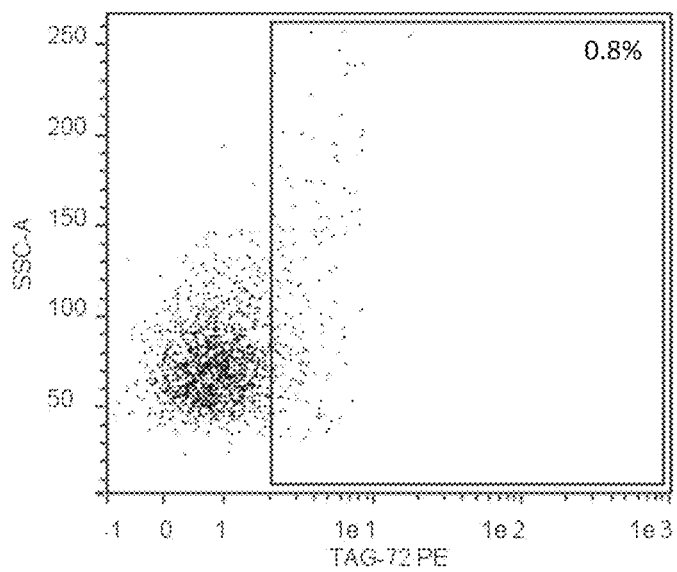

Examples of nucleic acid constructs encoding a CAR targeting TAG-72 are depicted in FIG. 4A, and exemplary sequences for CAR and various domains suitable for use in CARs are provided in SEQ ID NOS: 1-11.

| SEQ ID NO. | Description |
| --- | --- |
| 1 | DNA coding for TAG-72 scFV |
| 2 | Protein sequence of TAG-72 scFV |
| 3 | CD8 hinge protein sequence |
| 4 | CD8 TM protein sequence |
| 5 | CD28 hinge protein sequence |
| 6 | CD28 hinge protein sequence with C to S substitution |
| 7 | CD28 TM protein sequence |
| 8 | CD28 TM with C to S substitution |
| 9 | CD28 signalling domain protein sequence |
| 10 | 4-1BB signalling domain protein sequence |
| 11 | TCR zeta signalling domain protein sequence |
| 12 | TAG-72 VH CDR1 |
| 13 | TAG-72 VH CDR2 |
| 14 | TAG-72 VH CDR3 |
| 15 | TAG-72 VL CDR1 |
| 16 | TAG-72 VL CDR2 |
| 17 | TAG-72 VL CDR3 |

Expression Vector/Constructs—A construct or vector for expressing a CAR in a recipient cell can comprise one or more DNA regions comprising a promoter operably linked to a nucleotide sequence encoding a CAR and, optionally, a second DNA region encoding a selectable marker. The promoter can be inducible or constitutive. Examples of suitable constitutive promoters include, e.g., an immediate early cytomegalovirus (CMV) promoter, an Elongation Growth Factor-la (EF-la) gene promoter, a simian virus 40 (SV40) early promoter, a mouse mammary tumor virus (MMTV) promoter, a human immunodeficiency virus (HIV) long terminal repeat (LTR) promoter, a MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Examples of inducible promoters include, but are not limited to a metallothionine promoter, a glucocorticoid promoter, a progesterone promoter, and a tetracycline promoter.

The expression constructs may be generated by any suitable method including recombinant or synthetic techniques, utilizing a range of vectors known and available in the art such as plasmids, bacteriophage, baculovirus, mammalian virus, artificial chromosomes, among others. The expression constructs can be circular or linear, and should be suitable for replication and integration into eukaryotes. Viruses, which are useful as vectors include, but are not limited to, retroviruses, adenoviruses, adeno-associated viruses, herpes viruses and lentiviruses. A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to the subject stem cells. A number of retroviral systems are known in the art.

CAR-Expressing Cells—A CAR-encoding expression vector can be readily introduced into a host cell (e.g., a T cell or an NK cell) by physical, chemical, or biological means. Physical methods for introducing a polynucleotide into a host cell include calcium phosphate precipitation, lipofection, particle bombardment, microinjection, electroporation, and the like. Biological methods for introducing a viral vector into a host mammalian cell are widely used. Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle is a liposome (e.g., an artificial membrane vesicle). The cells used herein, e.g., T cells and NK cells, can be obtained from human subjects, either normal healthy individuals or the individual to be treated, using known methods. The cells used herein, e.g., T cells and NK cells, can also be generated by the differentiation of stem cells, e.g., induced pluripotent stem cells (iPSCs), derived by re-programming cells obtained from donor individuals. The resulting cells harboring a CAR-encoding expression polynucleotide, can be assessed prior to clinical use, e.g., assessment in respect of expression of CAR, recognition and killing of TAG-72 expressing target cells in vitro.

Treatment and Administration

In accordance with this disclosure, a TAG-72 targeting agent disclosed herein can be administered to a patient suffering from TCL, in particular CTCL, such as SS to treat the cancerous condition.

The term "treatment" refers to effective inhibition (e.g., slowing down or elimination) of the growth and/or metastasis of the cancer.

A TAG-72 targeting agent disclosed herein can be administered systemically (e.g., via a parenteral route such as an intravenous, intraperitoneal, intradermal, subcutaneous or intramuscular route), or via direct injection into a cutaneous lesion(s). The dosage of an agent to be administered depends on the nature of the agent, the stage of the cancer, and other clinical factors (such as weight and condition of the subject, the type of formulations and the route of administration). The precise dosage to be therapeutically effective and non-detrimental can be determined by those skilled in the art.

In some embodiments, the treatment is directed to a TCL patient who has been identified as having an increased level or proportion of TAG-72 expressing T cells in the blood. By "an increased level", it is meant that the level of TAG-72 expressing T cells in a patient is significantly higher, e.g., at least 50%, 75%, 100%, 2 fold, 3 fold, 4 fold, 5 fold, 6 fold, 7 fold, 8 fold, 9 fold, 10 fold, or higher, than that in healthy individuals (i.e., control level). The level can be determined based on the percentage of T cells in the blood that are TAG-72 positive, which can be identified by, e.g., FACS analysis using surface antigen staining for T-cell markers (e.g., CD3, CD4, CD5, CD7, or CD45RO, or a combination thereof) and staining for TAG-72. Alternatively, soluble TAG-72 in the plasma or serum of CTCL patients may be detected by standard techniques (such as ELISA).

Accordingly, also disclosed herein is a method of classifying or subtyping TCL patients by determining the level of TAG-72 expressing T cells in the patient blood and/or the presence of soluble TAG-72 in the plasma or serum. Those patients having an increased level of TAG-72 expressing T cells in the blood or increased levels of soluble TAG-72 are believed to be responsive to a treatment based on a TAG-72 targeting agent disclosed herein.

The TAG-72 specific treatment disclosed herein can be combined with other treatment of TCL and, in particular, CTCL. Current treatment selection for CTCL typically depends on the extent of skin involvement, the type of skin lesion, and whether the cancer has spread to the lymph nodes or other internal organs, and can be either directed at the skin or systemic. Existing skin-directed therapies are useful for patch and limited plaque disease and include topical treatments such as corticosteroids, retinoids, or imiquimod (which activates immune cells), mechlorethamine gel (Valchlor), topical chemotherapy, local radiation, methotrexate, photopheresis, ultraviolet light (phototherapy). Mechlorethamine is also approved as an intravenous treatment.

The present description is further illustrated by the following examples, which should not be construed as limiting in any way. The contents of all cited references (including literature references, issued patents, and published patent applications as cited throughout this application) are hereby expressly incorporated by reference.

Example 1—Identification of TAG-72+ T Cells in the Blood of Patients with SS by FACS Whole blood from donors diagnosed with SS was obtained by venepuncture and collected into Acid Citrate Dextrose (ACD) tubes. Peripheral blood mononuclear cells (PBMCs) were separated by Ficoll density centrifugation and resultant cells were characterized immediately or cryopreserved.

In brief, isolated patient PBMCs were incubated with 8-colour antibody cocktail at 4° C., 15 min ($1\times10^7$ cells/100 uL) protected from light. Cells were washed twice with FACS buffer before resuspending in a final volume of 200 uL. Flow cytometric analysis was performed on a MACSQuant analyzer (Miltenyi Biotec). Data analysis was carried out using FlowLogic software.

T cells were analyzed by FACS analysis, using surface antigen staining for CD3, CD4, CD5, CD7, and CD45RO, or for CD3 alone, in conjunction with analysis for TAG-72 expression (FIGS. 1A-1M and FIG. 2). Analysis of additional surface antigens such as CD2, CD30, CD158k, CLA and CCR4 may also be implemented in the characterization of the SS phenotype.

Figure 2:
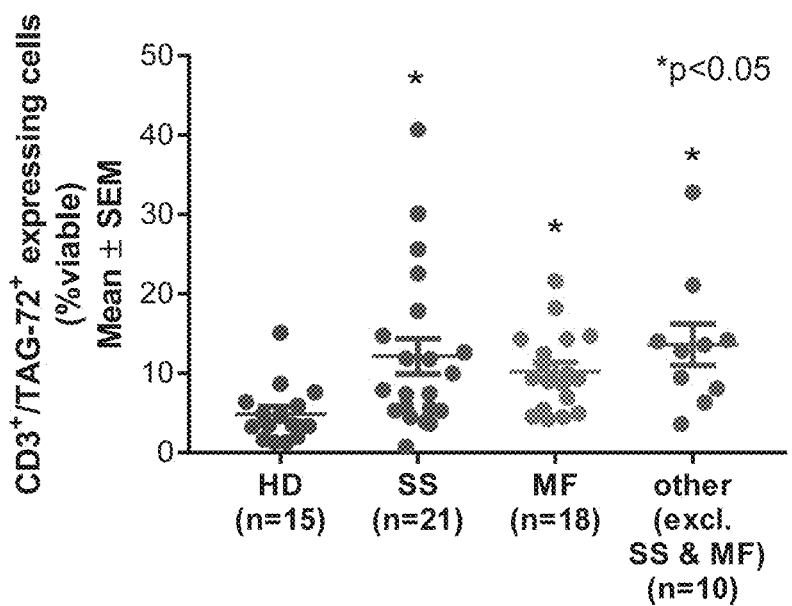
FIG. 2. Patients with different forms of TCL show an increased frequency of TAG-72+ T cells compared with normal individuals. PBMCs were obtained from a total of 15 healthy donors (HD), 21 Sezary Syndrome (SS) patients, 18 mycosis fungoides (MF) patients and 8 patients with other forms of TCL (including anaplastic large-cell lymphoma, peripheral T cell lymphoma, and follicular trophic mycosis fungoides). TAG-72 is expressed to a significantly higher degree on the CD3+ T cell subset in SS (red), MF (green), and other forms of TCL (purple) PBMCs compared to healthy donor cells (blue) as demonstrated by flow cytometry (p<0.05). Figures represent population frequency as a percent of total events analysed (% T)±SEM. The gating strategy implemented electronically excluded cell debris and selected for single, viable cells. CD3+ cells were subsequently analysed for the co-expression of TAG-72.

The results from FIG. 2 are summarized in Table 1.

TABLE 1

Summary of percent TAG-72+ phenotype T cells in TCL patients compared to T cells from normal individuals.

| Donor | TAG-72+ T cells % viable | | | Mean ± SD (n) |
|---|---|---|---|---|
| Healthy | 3.45 | 3.37 | 1.32 | 5.7 ± 4.5 (15) |
|  | 4.8 | 7.6 | 3.5 |  |
|  | 3.28 | 6.39 | 15.09 |  |
|  | 4.8 | 1.31 | 8.68 |  |
|  | 1.96 | 5.89 | 1.65 |  |
| TCL | 40.7 | 7.36 | 5.73 | 11.7 ± 8.1 (49) |
|  | 11.16 | 14.73 | 7.44 |  |
|  | 14.3 | 5.33 | 11.86 |  |
|  | 12.62 | 25.59 | 13.58 |  |
|  | 0.73 | 12.45 | 7.89 |  |
|  | 3.62 | 6.94 | 14.69 |  |
|  | 5.61 | 9.49 | 8.97 |  |
|  | 11.77 | 18.24 | 12.81 |  |
|  | 4.46 | 9.93 | 14.04 |  |
|  | 5.29 | 5.39 | 14.19 |  |
|  | 3.89 | 4.92 | 21.59 |  |
|  | 14.32 | 9.31 | 21.1 |  |
|  | 8.05 | 8.69 | 17.85 |  |
|  | 6.31 | 9.36 | 30.1 |  |
|  | 4.53 | 4.22 | 3.65 |  |
|  | 22.58 | 4.49 | 32.81 |  |
|  | 9.97 |  |  |  |

While there is overlap in the frequency of TAG-72+ T cells between the healthy and TCL donors, the frequency is elevated in TCL patients. Table 2 shows an analysis of the data from Table 1, using a frequency of 10% is as a cut-off level between healthy and TCL donors.

TABLE 2

Percentage of TAG-72+ T cells above or below 10% of total viable T cells in PBMCs from healthy donors or TCL patients.

|  | <10% TAG-72+ | >10% TAG-72+ |
|---|---|---|
| Healthy donors | 14/15 [93.3%] | 1/15 [0.7%] |
| TCL patients | 27/49 [55.1%] | 22/49 [44.9%] |

The difference between the two groups is statistically significant [chi-square=7.2911, p=0.00693].

To determine whether TAG-72 could be detected on cells from leukemic patients, whole blood or bone marrow (BM) from T-ALL (n=5) and B-ALL (n=4) patients were obtained, where cells of interest were isolated using Ficoll density centrifugation as previously described. Resultant cells used for characterisation were cryopreserved. Isolated patient PBMCs or BM cells ($2\times10^5$ cells/test) were incubated with a combination of CD3, CD19 and TAG-72 fluorescently conjugated antibodies at 4° C. for 10 min, protected from light. Cells were washed twice with FACS buffer before resuspending in a final volume of 200 uL. Flow cytometric analysis was performed on the BD Symphony analyser (BD Biosciences). Data analysis was carried out using the FlowLogic software.

As shown in FIGS. 1N-1V, TAG-72 levels did not exceed baseline in T-ALL (N-R) or B-ALL (S-V) patient samples, suggesting that aberrant TAG-72 appears to only be associated with the T cells from TCL.

Example 2—Demonstration of TAG-72 Expression in Multiple Forms of TCL

PBMCs from TCL patients (including SS, non-SS CTCL and PTCL) and HD PBMCs were analysed for CD3 and TAG-72 expression using flow cytometry. PBMCs were isolated from whole blood using Ficoll density centrifugation as previously described. Resultant PBMCs were quantitated and an equivalent number of cells ($2\times10^5$ cells/100 µL) for each donor were incubated with anti-CD3 and anti-TAG-72 fluorophore-conjugated antibodies for 15 min, at 4° C., protected from light. Cells were washed twice with cold PBS before resuspending in a final volume of 200 µL. Propidium iodide was added to samples immediately before analysing. Samples were analysed using the MACSQuant (Miltenyi Biotec). Data analysis was carried out using FlowLogic software.

FIG. 2 shows that SS, non-SS CTCL and PCTL CD3+ T cells express TAG-72 at a significantly greater frequency than HD CD3+ T cells.

Example 3—Demonstration of Soluble TAG-72 in Plasma of CTCL Patients

Plasma samples were obtained from 29 CTCL patients (24SS and 5 mycosis fungoides) and 14 healthy donors. The samples were assayed for levels of soluble TAG-72 using a commercial ELISA kit operated in accordance with the manufacturer's product instruction sheet (IBL International, CA 72-4 ELISA, RE54111). Normal human AB serum was included as an additional normal control.

Figure 3A:
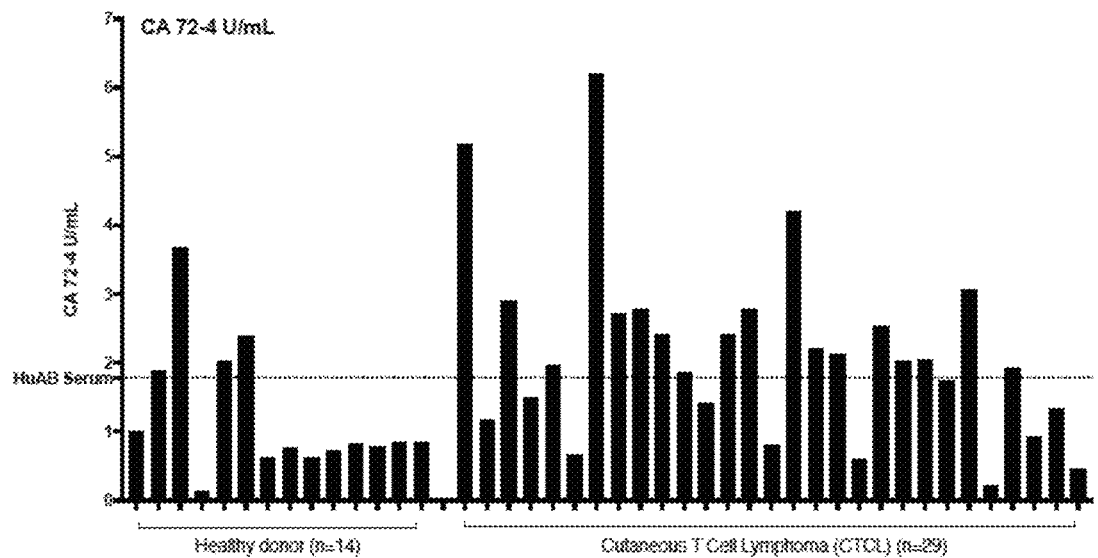
FIGS. 3A-3B. CTCL patients have significantly greater levels of soluble TAG-72 in their plasma than healthy donors. Plasma samples from 29 CTCL patients and 14 healthy donors were assessed for soluble TAG-72 by ELISA. Results for individual patients and donors are shown as bar graphs (A) and scatterplots (B). The mean level of TAG-72 in CTCL patients is significantly greater than the level in healthy donors (P<0.05). The dotted line indicates the level of TAG-72 detected in normal human AB serum.
Figure 3B:
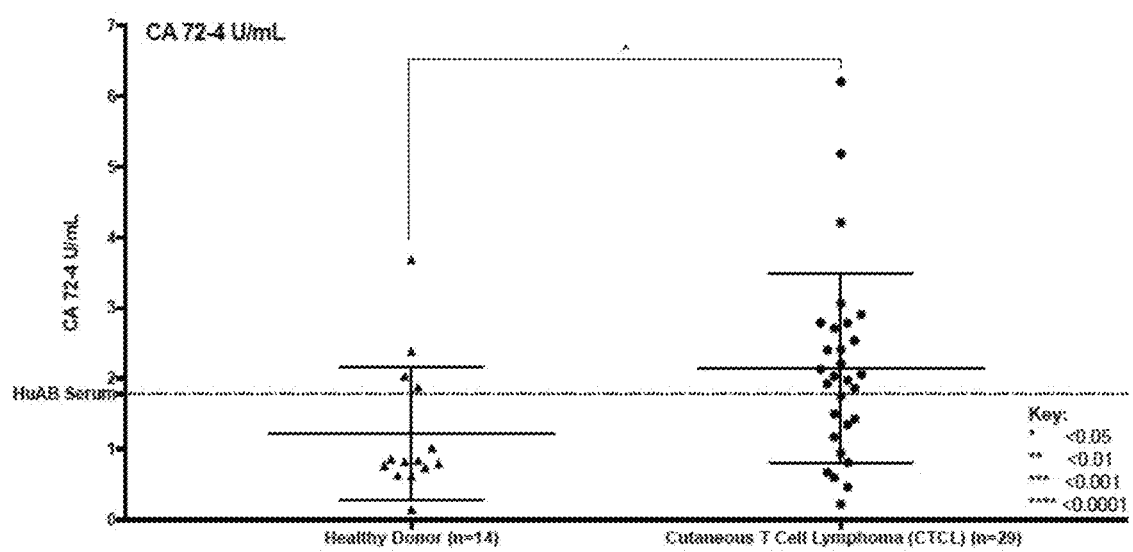

FIGS. 3A-3B shows that the levels of soluble TAG-72 in the plasma of CTCL patients were significantly greater than those in the plasma of healthy donors.

Example 4—Detection of TAG-72 Bearing Cells in Skin Biopsies from CTCL Patients Skin biopsies were obtained from 11 patients—5 SS, 3 MF, 1 anaplastic T cell lymphoma and 2 tentatively-diagnosed MF patients—and immediately formalin fixed. 4 um sections were cut from the biopsies and then stained by hematoxylin and eosin (H&E), or for expression of TAG-72 or CD3 (T cell marker) using standard immunohistochemistry techniques. Slides were scored as either positive or negative for TAG-72 or CD3 by an experienced histologist (blinded to the identity of the samples).

FIG. 4A shows sample microscopic fields (at 40× magnification) for each of the sections. Four of the patient samples were scored as positive for TAG-72 (patients 1, 2, 10 and 11), while all 10 of the 11 samples were scored positive for CD3 (with one sample not available). The presence of T cells in the skin of CTCL patients is well known. The presence of TAG-72 positive cells (co-localising with CD3 and therefore presumably TAG-72 positive T cells) has not previously been known. The frequency of detection of TAG-72 positive T cells in the skin of CTCL patients (36%) correlates well with the frequency of elevated levels of TAG-72 positive T cells in TCL patients (45%), as shown in Table 2, within the limitations of relatively small sample numbers.

FIG. 4B summarizes the expression of TAG-72 on infiltrating T cells and circulating T cells from matched donors where available. TAG-72 expression is not limited to one aspect of the disease phenotype, as both circulating and infiltrating T cells are recognised as TAG-72+ in 2/11 samples (where four samples are not available).

Example 5—Creation of CAR-T Cells Targeting TAG-72

CAR constructs targeting TAG-72 were generated and are graphically depicted in FIG. 5A. The CARs are each composed of a single-chain Fv (scFv) specific for TAG-72 having an amino acid sequence depicted in FIG. 5B. These CAR constructs were cloned into a lentiviral vector which were used for transduction of T cells. The results shown in subsequent Examples utilized either the TAG-72 (1) or the TAG-72 (3) constructs transduced into donor-derived T cells, to generate TAG-72 CAR (1) or TAG-72 CAR (3) T cells, respectively. The two constructs have the same TAG-72 scFv (SEQ ID NO: 2) but differ in their hinge, transmembrane and signaling domain sequences, as shown in FIG. 5A.

To make lentiviruses, 293T cells were plated onto poly-L-lysine (Sigma) coated 175 $cm^2$ flasks. Two hours prior to transfection, medium was replaced with DMEM supplemented with 10% FCS. The lentiviral transfer vector DNA, together with packaging and envelope plasmid DNA were combined and mixed with Lipofectamine2000. The solution was briefly vortexed and incubated at room temperature for 30 min. Following this, the solution was mixed again and then added dropwise to the cells. Flasks were returned to the incubator. Six hours later, fresh growth medium added. Viral supernatant was collected after 48 hrs and cleared by centrifugation at 1500 rpm for 5 min at 4° C. then passed through a 0.45 µm pore PVDF Millex-HV filter (Millipore). Concentration of lentivirus using ultracentrifugation was performed with a Sorval Discovery 100 SE centrifuge using an AH-629 rotor. 30 mL of filtered virus supernatant was added to 36 mL polyallomer conical tubes (Beckman). Centrifugation was performed for 90 min at 20,000 g. Supernatant was completely removed and virus pellets resuspended in 300 µL PBS and stored at −80° C. until use.

Optimal lentiviral transduction of T cells involves their activation at the TCR and co-stimulatory receptors. Accordingly, on day 0, fresh PBMC were collected by apheresis from healthy donors, were enriched for activated T cells with the use of anti-CD3 and anti-CD28 antibodies bound to paramagnetic beads (Dynabeads ClinExVivo CD3/CD28, Invitrogen, Camarillo, CA, USA) at a ratio of 3:1 (beads: cells). The cells and beads were co-incubated for 1 h at room temperature, and CD3+ cell enrichment was performed with the use of magnet (Invitrogen). Cells in the CD3+ fraction were resuspended in initiation media at a concentration of $1\times10^6$ cells/ml in T cell expansion medium with 100 IU/ml IL-2. On day 1, RetroNectin was used to coat cell culture dishes at a concentration of 2 mg/cm2 in a solution of 10 mg/mL in PBS overnight at 4° C. On day 2, the RetroNectin solution was aspirated and the same volume of blocking solution, consisting of 0.5% human serum albumin in PBS, was added to each dish and incubated at room temperature for 30 min. The blocking solution was aspirated, and each dish washed with PBS. Lentiviral supernatant was rapidly thawed and added to each dish with T cell expansion medium with 300 IU/ml IL-2. The cultures were placed back into the incubator and left for at least 24 h. On day 4, the transduction was stopped; cells were resuspended in fresh T-cell expansion medium at a concentration of $0.5\text{-}1\times10^6$ cells/mL. The cultures were maintained until day 14 and fed every other day with fresh expansion media to maintain cell concentration at 1×10⁶ cells/mL.

Example 6—Specific Killing of TAG-72+ Adherent Cell Lines In Vitro Using TAG-72-Targeted CAR-T Cells The real-time cell monitoring system (xCELLigence) was employed to determine the killing efficiency of CAR-T cells in vitro. 10,000 target cells/100 µL (for example the ovarian cancer cell line Ovcar3) were resuspended in culture media (for example, RPMI-1640 media) supplemented with 10%-20% fetal calf serum and deposited into RTCA plates. Target cells were maintained at 37° C., 5% $CO_2$ for 3-20 h to allow for cellular attachment. Following attachment of target cells, TAG-72-specific CAR-T effector cells from Example 3 were added at variable effector to target ratios ranging from 1:5 to 5:1. In some instances, effector cells were isolated based on GFP or FLAG expression via FACS prior to use. Co-cultures were maintained in optimal growth conditions for at least 12 h. Throughout, cellular impedance was monitored; a decrease in impedance is indicative of cell detachment and ultimately cell death.

TAG-72 CAR (1) and TAG-72 CAR (3) T cells mediated potent cell killing of TAG-72$^{hi}$ expressing target cancer cells (Ovcar 3) but not TAG-72$^{-ve/low}$ cancer target cells (MESov) (FIGS. 6A-6D).

Example 7—Specific Killing of TAG-72+ Non-Adherent Jurkat Cells In Vitro Using TAG-72-Targeted CAR-T Cells The T cell leukemic cell line, Jurkat, was confirmed as a TAG-72 expressing cell line using flow cytometry. Jurkat cells are non-adherent and hence represent a good model for testing cells from SS patients. Jurkat cells were co-cultured with TAG-72 CAR-T (1), TAG-72 CAR (3) or non-transduced (NT) PBMCs from the same donor at an effector to target ratio of 5:1. In some instances, effector cells were isolated based on GFP or FLAG expression via FACS prior to use. Cultures were maintained at 37° C., 5% $CO_2$ for 48 h. At this time, co-cultures were again analyzed by flow cytometry for TAG-72 expression. In addition, Annexin and PI staining was performed to distinguish dead from early apoptotic cells in the co-culture. Given CAR-T cells do not express TAG-72, it was possible to distinguish between target and effector cell death in the FACS analysis.

FIGS. 7A-7E show that Jurkat cells express TAG-72 and can be killed in suspension culture in vitro by CAR-T cells that target TAG-72.

Example 8—Killing of T Cells from Patients with Sezary Disease In Vitro Using TAG-72-Targeted CAR-T Cells SS patient PBMCs were used immediately after isolation from whole blood or thawed from frozen stock on the day of use. TAG-72 CAR-T (1) effector cells were added to patient PBMCs at an effector to target ratio of 5:1 in a multi-well plate. In some instances, effector cells were isolated based of GFP or FLAG expression via FACS prior to use. Cell suspensions were maintained in T cell expansion media supplemented with human serum at 37° C., 5% $CO_2$ for 48 h at which point phenotypic analysis was performed. Staining for TAG-72 was performed at 4° C. for 15 min (1×10⁷ cells/100 uL) protected from light. Cells were washed twice with FACS buffer before resuspending in a final volume of 200 uL. Flow cytometric analysis was performed on MACSQuant (Miltenyi Biotec). Data analysis was carried out using FlowLogic software. Healthy donor PBMCs were maintained and analysed in parallel.

FIGS. 8A-8E show that the percentage of TAG-72+ cells within the lymphocyte population of SS patient PBMCs are significantly reduced following 48 h exposure to TAG-72 CAR (1) T cells in vitro.

Example 9—Killing of T Cells from Patients with CTCL In Vitro Using TAG-72 CAR (3) T Cells SS patient PBMCs were used immediately after isolation from whole blood or thawed from frozen stock on the day of use. TAG-72 (3) CAR-T effector cells (CAR-T cells containing the 4-1ββ intracellular signaling domain, without GFP reporter) were added to patient PBMCs at an effector to target ratio of 5:1 in a multi-well plate. Cell suspensions were maintained in T cell media supplemented with human serum at 37° C., 5% $CO_2$ for 24 h, at which point phenotypic analysis was performed. Staining for TAG-72 and CD3 was performed at 4° C. for 15 min (2×10⁵ cells/test) protected from light. Cells were washed twice before resuspending in a final volume of 200 uL. Flow cytometric analysis was performed using the MACSQuant (Miltenyi Biotec). Data analysis was carried out using FlowLogic. Healthy donor PBMCs were maintained and analyzed in parallel. CAR-T cells generated from T cells obtained from three independent healthy donors were used, demonstrating that the killing ability of the CAR-T cells was not donor-dependent.

FIGS. 9A-9H demonstrate that the frequency of TAG-72+ T cells are reduced following 24 h exposure to TAG-72 (3) T cells in vitro.

Example 10—Killing of TAG-72+ Cells Using an Anti-TAG-72 Antibody-Drug Conjugate SS patient and normal control donor PBMCs were separated from whole blood using Ficoll density centrifugation. Resultant cells were used immediately or thawed from frozen stock on day of use. Cell suspensions were maintained in T cell expansion media supplemented with 5% human AB serum and 20 U IL-2 at 37° C., 5% $CO_2$. Cells were exposed to the anti-TAG-72 antibody-drug conjugate CC49-DM1 for 48 h, at which point phenotypic analysis was performed to determine the level of TAG-72+ cells remaining within the SS subpopulation (CD3⁺/CD4⁺/CD7$^{neg}$/CD45RO⁺), and normal PBMCs relative to untreated controls. The TAG-72 expressing T cell leukemic cell line, Jurkat, was analyzed in parallel, where changes in total viable TAG-72+ cells were monitored.

FIGS. 10A-10E show that the TAG-72 antibody-drug conjugate was able to substantially reduce the percentage of TAG-72+ cells in PBMCs from SS patients and in cultured Jurkat cells. No effect was seen on PBMCs from healthy donors.

What is claimed is:

1. A method of treating a T cell lymphoma (TCL) in a patient, wherein the TCL comprises T cells displaying increased expression of tumor-associated glycoprotein-72 (TAG-72) relative to healthy donor T cells, wherein the method comprises administering an agent targeting TAG-72 to the patient.

2. The method of claim 1, wherein the agent comprises an antibody, or an antigen binding fragment thereof, specific for TAG-72.

3. The method of claim 2, wherein the antibody or antigen-binding fragment is conjugated to a cytotoxic agent.

4. The method of claim 3, wherein the cytotoxic agent is a small molecule compound.

5. The method of claim 2, wherein the antibody mediates antibody-dependent cell mediated cytotoxicity (ADCC) activity.

6. The method of claim 5, wherein the antibody is a bispecific antibody.

7. The method of claim 6, wherein the bispecific antibody binds to a receptor on a T cell, an NK cell, an NKT cell, a MAIT cell, or a macrophage.

8. The method of claim 1, wherein the agent comprises a cell expressing a chimeric antigen receptor (CAR) comprising an antigen recognition moiety specific for TAG-72.

9. The method of claim 8, wherein the cell expressing the CAR is a T cell.

10. The method of claim 9, wherein the T cell is selected from the group comprising: γδ T-cell receptor (TCR) T cell, αβ TCR T cell, natural killer T (NKT) cell, and Mucosal associated invariant T (MAIT) cell.

11. The method of claim 8, wherein the cell expressing the CAR is a natural killer (NK) cell.

12. The method of claim 8, wherein the antigen recognition moiety comprises a single-chain variable fragment (scFv) comprising:
    six complementarity determining regions (CDRs); wherein CDR1-H has the amino acid sequence of SEQ ID NO: 12, CDR2-H has the amino acid sequence of SEQ ID NO: 13, and CDR3-H has the amino acid sequence of SEQ ID NO: 14; and CDR1-L has the amino acid sequence of SEQ ID NO: 15, CDR2-L has the amino acid sequence of SEQ ID NO: 16, and CDR3-L has the amino acid sequence of SEQ ID NO: 17.

13. The method of claim 8, wherein the CAR comprises the intracellular signaling domain of cluster of differentiation 3 (CD3)-zeta.

14. The method of claim 13, wherein the CAR further comprises the intracellular costimulatory domain of CD28, 4-1 BB, or CD2.

15. The method of claim 8, wherein the antigen recognition moiety comprises an scFv comprising a heavy chain variable region (VH) comprising an amino acid sequence of Q1 to S115 of SEQ ID NO: 2; and a light chain variable region (VL) comprising an amino acid sequence of D131 to R244 of SEQ ID NO: 2.

16. The method of claim 8, wherein the antigen recognition moiety comprises an scFv comprising the amino acid sequence of SEQ ID NO: 2.

17. The method of claim 1, wherein the TCL is T-lymphoblastic lymphoma, peripheral T cell lymphoma, cutaneous T cell lymphoma, adult T cell lymphoma, angioimmunoblastic T cell lymphoma, extranodal natural killer/T cell lymphoma (nasal type), enteropathy-associated intestinal T cell lymphoma (EATL), Sezary Syndrome, anaplastic large-cell lymphoma, erythrodermic mycosis fungoides or follicular trophic mycosis fungoides.

18. The method of claim 1, wherein the patient has been identified as having an increased level of TAG-72 expressing T cells or soluble TAG-72 in the blood prior to the treatment.

* * * * *